(12) United States Patent
Ganem et al.

(10) Patent No.: US 7,832,399 B2
(45) Date of Patent: Nov. 16, 2010

(54) MEDICATION INHALER

(75) Inventors: Charles F. Ganem, Cape Neddick, ME (US); Jake Ganem, Cape Neddick, ME (US); Scott Ganem, Portsmouth, NH (US)

(73) Assignee: One Dose, LLC, Cape Neddick, ME (US)

( * ) Notice: Subject to any disclaimer, the term of this patent is extended or adjusted under 35 U.S.C. 154(b) by 920 days.

(21) Appl. No.: 11/716,204

(22) Filed: Mar. 9, 2007

(65) Prior Publication Data

US 2007/0221216 A1 Sep. 27, 2007

Related U.S. Application Data

(60) Provisional application No. 60/781,265, filed on Mar. 10, 2006.

(51) Int. Cl.
*A61M 15/00* (2006.01)
(52) U.S. Cl. ............... 128/203.21; 128/203.12; 128/203.15; 128/203.23; 604/58
(58) Field of Classification Search ........... 128/200.21, 128/203.12, 203.15, 203.21, 203.23, 203.24; 222/80; 604/23, 24, 26, 57, 58, 272, 273, 604/274
See application file for complete search history.

(56) References Cited

U.S. PATENT DOCUMENTS

| 1,406,903 | A | * | 2/1922 | Rose ................... 222/82 |
| 2,307,986 | A | * | 1/1943 | Brown et al. .............. 604/58 |
| 4,014,336 | A | * | 3/1977 | Mathes ................ 128/203.15 |
| 4,045,525 | A | * | 8/1977 | Huggins .................. 261/124 |
| 4,116,195 | A | * | 9/1978 | James ..................... 604/244 |
| 4,338,931 | A | | 7/1982 | Cavazza |
| 4,423,724 | A | | 1/1984 | Young |
| 5,048,514 | A | | 9/1991 | Ramella |
| 5,263,475 | A | | 11/1993 | Altermatt et al. |
| 5,372,128 | A | * | 12/1994 | Haber et al. ........... 128/203.21 |
| 5,647,349 | A | | 7/1997 | Ohki et al. |
| 5,715,811 | A | | 2/1998 | Ohki et al. |
| 5,848,994 | A | * | 12/1998 | Richmond ................ 604/248 |
| 5,868,721 | A | | 2/1999 | Marinacci et al. |
| 6,186,141 | B1 | * | 2/2001 | Pike et al. ............ 128/203.12 |
| 6,280,424 | B1 | * | 8/2001 | Chang et al. ............. 604/272 |
| 6,488,027 | B1 | | 12/2002 | Moulin |
| 6,613,026 | B1 | * | 9/2003 | Palasis et al. ............. 604/272 |

(Continued)

*Primary Examiner*—Steven O Douglas
*Assistant Examiner*—LaToya Louis
(74) *Attorney, Agent, or Firm*—Davis & Bujold, P.L.L.C.

(57) ABSTRACT

A medication inhaler having an inhaler body with a medication container chamber for receiving a medication container and at least one air passage connecting the medication container chamber with external air and a mouthpiece axially engageable with the inhaler body and having a mouthpiece chamber for communication with a patient's respiratory system and a hollow medication delivery needle communicating with the mouthpiece chamber. The medication delivery needle extends toward the medication container chamber and has at least one opening for passing exterior air and medication from an interior space of a medication container in the medication container chamber through the needle and to mouthpiece chamber. The mouthpiece engages with the inhaler body in a first position wherein the needle extends into the medication container chamber short of the medication container in the medication container chamber and in a second position wherein the needle axially traverses the medication container so that the at least one opening in the needle communicates with the at least one air passage and the interior space of the medication container in the medication container chamber.

14 Claims, 16 Drawing Sheets

U.S. PATENT DOCUMENTS

| | | |
|---|---|---|
| 6,637,430 B1 | 10/2003 | Voges et al. |
| 6,766,799 B2 | 7/2004 | Edwards et al. |
| 6,892,727 B2 | 5/2005 | Myrman |
| 6,923,175 B2 | 8/2005 | Poole et al. |
| 6,941,947 B2 | 9/2005 | Young et al. |
| 6,945,953 B2 | 9/2005 | Wright |
| 6,983,748 B2 | 1/2006 | Brown et al. |
| 7,645,268 B2 * | 1/2010 | Mickley et al. ............. 604/274 |
| 7,666,172 B2 * | 2/2010 | Atil ............................ 604/272 |
| 2003/0101995 A1 * | 6/2003 | Yamashita et al. ..... 128/203.15 |
| 2003/0163099 A1 * | 8/2003 | Wermeling et al. ......... 604/275 |
| 2003/0187404 A1 | 10/2003 | Waldenburg |
| 2005/0238708 A1 | 10/2005 | Jones et al. |
| 2006/0254583 A1 * | 11/2006 | Deboeck et al. ........ 128/203.15 |
| 2006/0283448 A1 * | 12/2006 | Edwards et al. ........ 128/203.15 |
| 2009/0090362 A1 * | 4/2009 | Harmer et al. ......... 128/203.21 |

* cited by examiner

| SIZE | OUTER DIAMETER (mm) | HEIGHT OR LOCKED LENGTH (mm) | ACTUAL VOLUME (mL) | TYPICAL FILL WEIGHTS (mg) 0.70 POWDER DENSITY |
|---|---|---|---|---|
| 000 | 9.91 | 26.14 | 1.37 | 960 |
| 00 | 8.53 | 23.30 | 0.95 | 665 |
| 0 | 7.65 | 21.70 | 0.68 | 475 |
| 1 | 6.91 | 19.40 | 0.50 | 350 |
| 2 | 6.35 | 18.00 | 0.37 | 260 |
| 3 | 5.82 | 15.90 | 0.30 | 210 |
| 4 | 5.31 | 14.30 | 0.21 | 145 |
| 5 | 4.91 | 11.10 | 0.13 | 90 |

EMPTY HARD GELETIN CAPSULE PHYSICAL SPECIFICATIONS

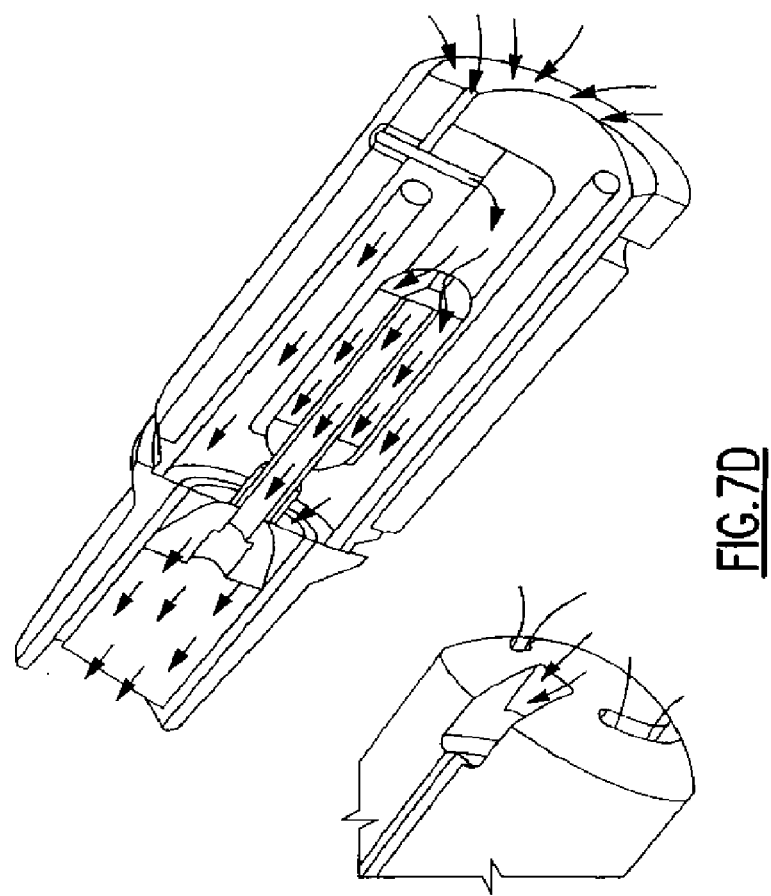
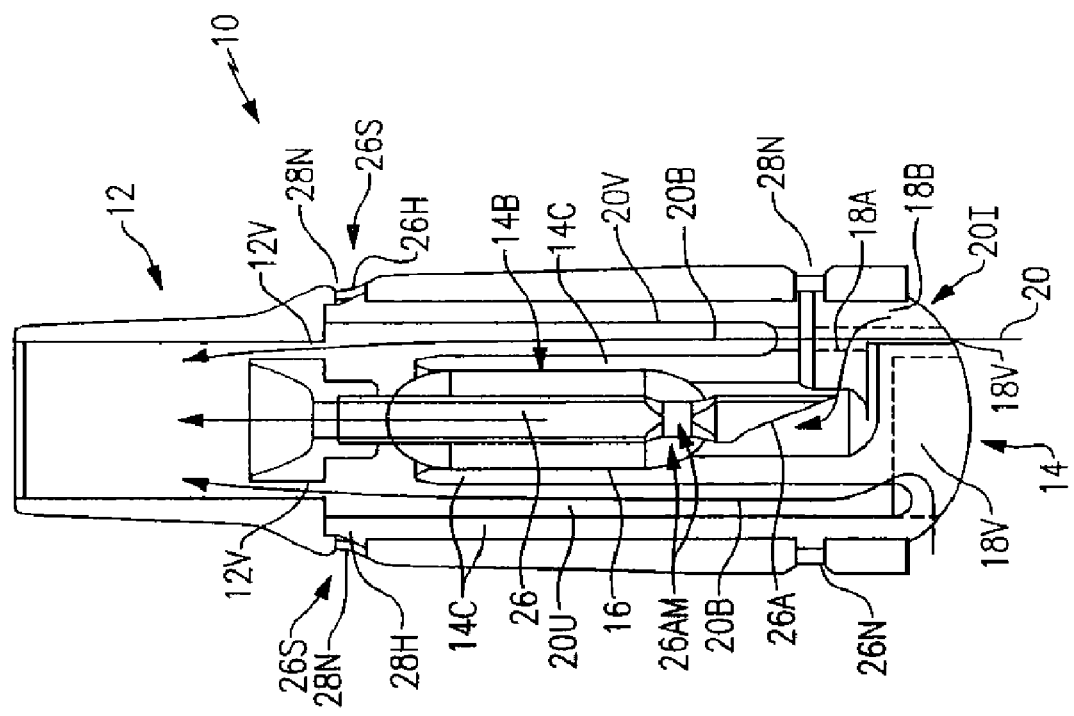
FIG.7D
FIG.7C

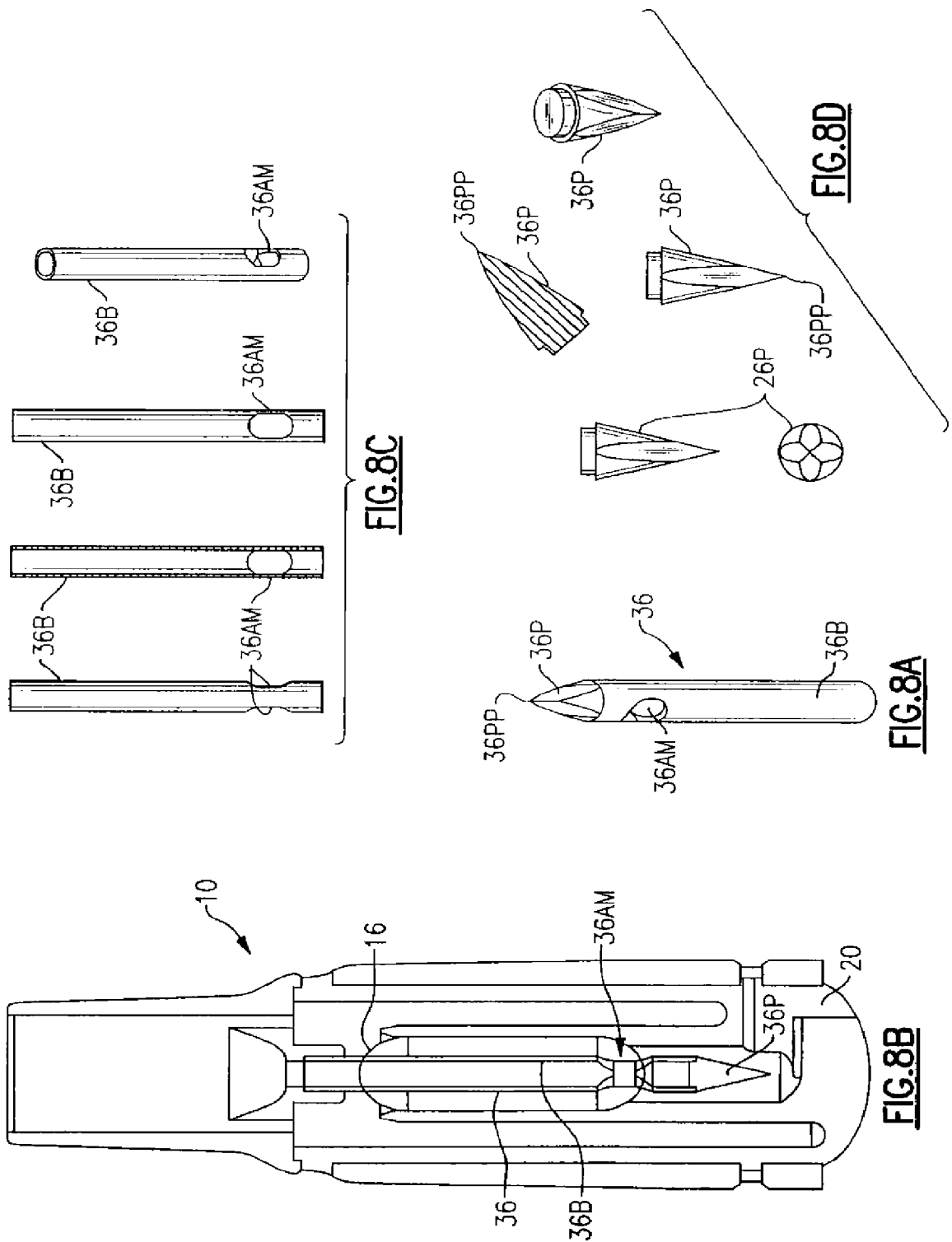

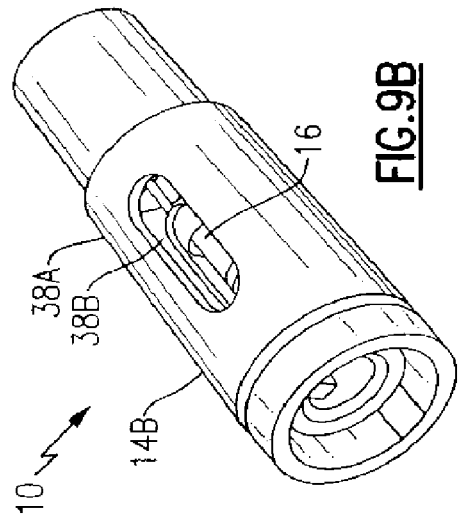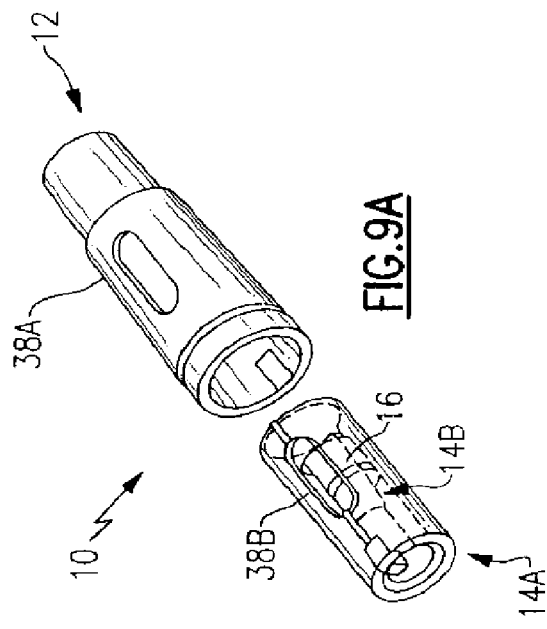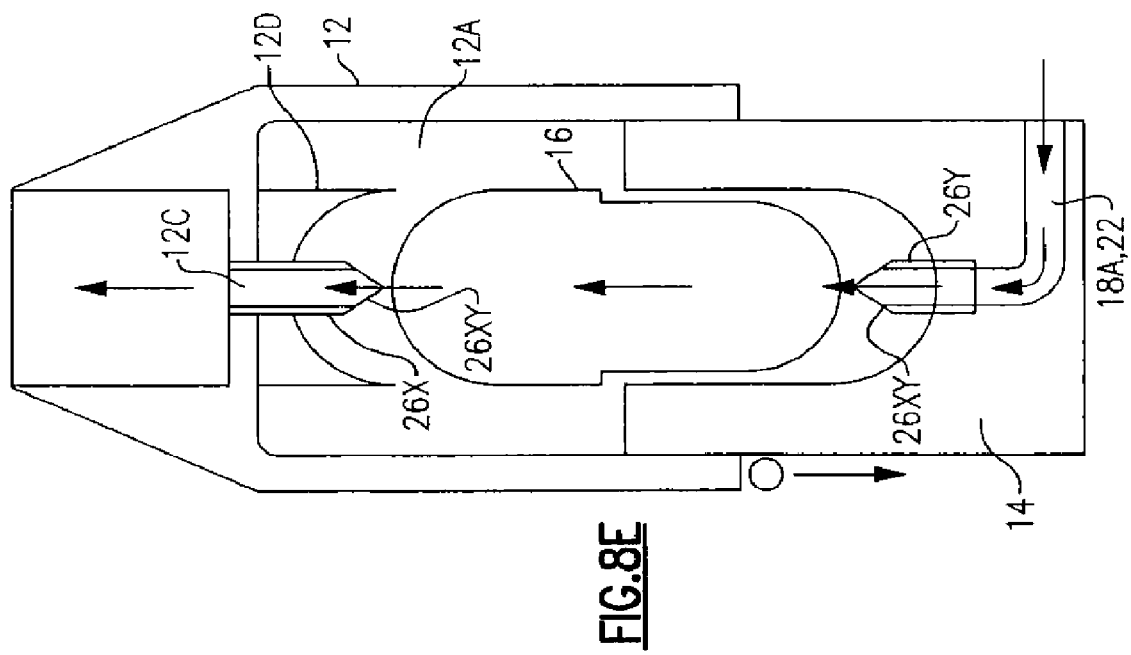

MEDICATION INHALER

This application is a continuation in part of U.S. Provisional Application Ser. No. 60/781,265 filed on Mar. 10, 2006.

FIELD OF THE INVENTION

The present invention relates to an apparatus for administering medication in the form of a dry powder or a wet medication formulated to as a "dry" medication wherein the medication is formulated to be inhaled and, in particular, to an inhalation dispenser enclosing a sealed capsule of dry powdered or wet medication formulated as a "dry" medication with an air passage mechanism providing access to the capsule contents and an inhalation passage for inhalation of a mixture of air and the dry powder contents of the capsule.

BACKGROUND OF THE INVENTION

There are many medications that are formulated to be inhaled, including medications for respiratory diseases and problems and medications that are more easily and rapidly absorbed through the respiratory tissues. Such medications are often formulated as "mists", that is, aerosols of droplets suspended in air, but may also be in the form of fine, dry powders.

There are various forms of inhalers designed for the administration of such medications, but each offers a number of problems. For example, both wet and dry inhalers must incorporate features that provide safe, long term storage for the medications before they are used, typically by encapsulation of the medications in cartridges or capsules that are loaded into the devices when the medications are to be used. The encapsulated medications must then be "opened" safely and in a manner compatible with the dispensing of the medications, which requires that the medications continue to be retained within the capsule or container, but in such a way as to allow the medication to be dispensed to the patient.

The opening of a medication cartridge or capsule and the extraction of the medication may present particular problems, depending upon the type of medication and the type of cartridge or capsule. For example, cartridges or capsules containing wet medications commonly contain a pressurized propellant. The capsule seal must therefore safely and reliably retain the pressurized contents during storage, which in itself will typically make the seal more difficult to open, and further requires that the capsule seal and the opening mechanism be designed so as to retain the pressurized contents when the seal is breached during the opening process, which present additional difficulties.

Dry medications, however, present a different set of equally difficult requirements and dry powder inhalers of the prior art have employed a number of different types of medication containers, such as blister packs and reservoir storage mechanisms, all of which have been unsatisfactory in one aspect or another. More recent dry powder inhalers of the prior art have employed gelatin capsules, which share certain problems of the other prior art medication containers, such as a tendency for the medications to "clump" and thus be difficult to release from the container, and which present problems particular to gelatin capsules and similar medication containers. For example, one of the major problems of gelatin capsules has been the flaking or shearing of capsule particulate, that is, the production of particles or dust of the capsule material during puncture or destruction of the capsule to gain access to the medication therein. While the capsule material particulate is typically too large to be inhaled into the patient's lungs, the particulate often enters the patient's throat and causes at least some degree of discomfort. This problem is in some respects somewhat analogous to the problem of "coring" in hypodermic needles wherein a hypodermic needle may "core" out a cylinder or plug of tissue when inserted into the body of a patient, rather than opening a passage into the tissue, and wherein as a consequence the freed cored tissue may block the passage through the needle.

For these reasons, among others, inhalers tend to be relatively complex devices that are correspondingly often difficult to use and are generally relatively expensive to manufacture. These characteristics in turn largely limit the common use of medication inhalers to regions or countries of relatively high economic and educational levels where they will be administered and used by relatively highly qualified and trained medical personnel and by relatively highly educated patients able to afford and effectively use such devices. There is a significant need, however, for relatively inexpensive, easy to use medication inhalers in economically limited regions of the world and by people, including medical personnel, of relatively low educational levels, and preferably of a single use, throw away form having significantly reduced storage and use requirements.

The present invention addresses these and other problems of the prior art.

SUMMARY OF THE INVENTION

The present invention is directed to an apparatus for administering medication in the form of a dry powder or a wet medication formulated to as a "dry" medication wherein the medication is formulated to be inhaled and, in particular, to an inhalation dispenser enclosing a sealed medication container of dry powdered or wet medication formulated as a "dry" medication with an air passage mechanism providing access to the medication container contents and an inhalation passage for inhalation of a mixture of air and the dry powder contents of the medication container.

In particular, the present invention is directed to a dry medication inhaler that includes an inhaler body having a medication container chamber for receiving a medication container and at least one air passage connecting the medication container chamber with external air and a mouthpiece axially engageable with the inhaler body and having a mouthpiece chamber for communication with a patient's respiratory system and a hollow medication delivery needle communicating with the mouthpiece chamber. According to the present invention, the medication delivery needle extends toward the medication container chamber and has at least one opening for passing exterior air and medication from an interior space of a medication container in the medication container chamber through the needle and to mouthpiece chamber.

The mouthpiece engages with the inhaler body in a first position wherein the needle extends into the medication container chamber short of the medication container in the medication container chamber and in a second position wherein the needle axially traverses the medication container so that the at least one opening in the needle communicates with the at least one air passage and the interior space of the capsule in the medication container chamber.

The dry medication inhaler may also include a detent mechanism for retaining the mouthpiece and inhaler body in the first position for storing the inhaler with a medication container loaded into the medication container chamber and in the second position when the inhaler is actuated to delivery medication to the patient's respiratory system.

In one embodiment of the present invention, the medication delivery needle is a hollow cylindrical body terminating in a puncture point formed at an end of the needle toward the medication container chamber. A puncture plane extends obliquely across a diameter of the cylindrical body at an end of the needle toward the medication container to define the puncture point at the end of the needle and puncture edges extending along the plane of intersection between the puncture plane and the cylindrical body. The puncture edges form an oval opening into the interior of the needle and include cutting edges extending from the puncture point for a first part of the puncture edges and anti-coring edges for a second part of the puncture edges. When the mouthpiece and inhaler body are moved from the first position to the second position the puncture point establishes an initial opening through a wall of the medication container, the cutting edges penetrate the wall of the medication container and separate a attached flap of medication container material from the medication container wall, and the anti-coring edges contact the medication container wall and push the attached flap of medication container aside, thereby forming an opening through the medication container wall wherein the wall material of the opening remains as a flap attached to the medication container wall.

The medication delivery needle may also have at least one air/medication port located along the medication needle such that when the mouthpiece and inhaler body are in the second position the a first part of a length of the air/medication ports is located within the medication container and a second part of the length of the air/medication ports is located in connection with the air passage connecting the medication container chamber with the exterior air. In certain embodiments the medication needle may have one or more pairs of diametrically opposed air/medication ports.

In further aspects of the invention, the inhaler body may include at least one body vent passage located between the medication container chamber and an outer surface of the inhaler body and connected to the exterior air and the mouthpiece may include at least one mouthpiece passage communicating between the at least one body vent passage and the mouthpiece chamber to provide a flow of exterior air into the mouthpiece chamber.

BRIEF DESCRIPTION OF THE DRAWINGS

The above discussed aspects of the prior art and the following discussed aspects of the present invention are illustrated in the figures, wherein:

FIGS. 7A-7D are diagrammatic illustrations of one presently preferred embodiment of the present invention with a first embodiment of a medication delivery needle;

FIGS. 8A-8E illustrate further embodiments of a medication delivery needle and inhaler;

FIGS. 9A and 9B illustrate an inhaler having container windows;

DETAILED DESCRIPTION OF THE INVENTION

A. Description of an Embodiment of a Dry Medication Inhaler

Figure 1A:
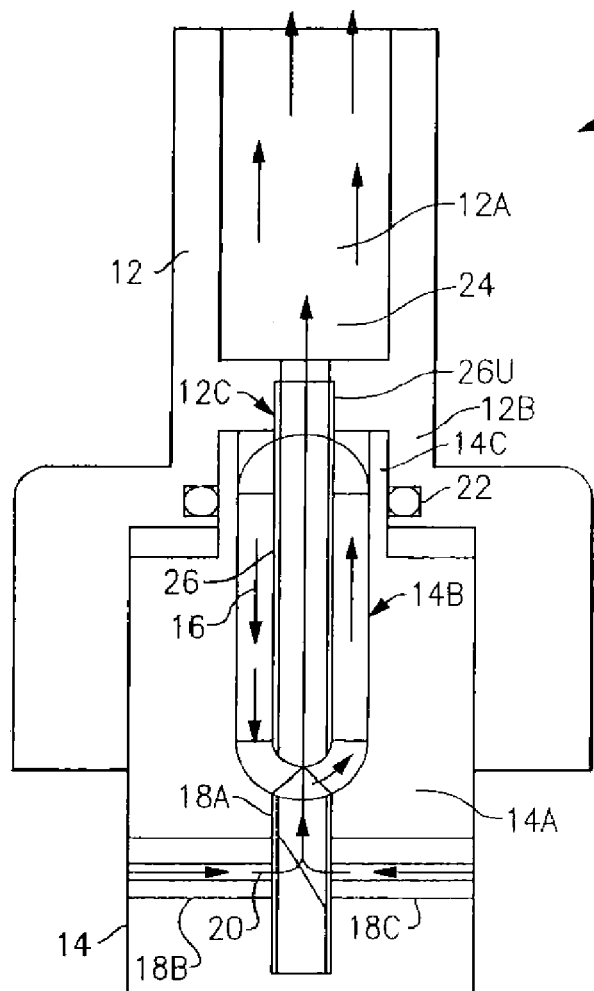
FIG. 1A is a diagrammatic representation of a dry medication inhaler.

Referring to FIG. 1A, therein is shown a diagrammatic representation of a dry medication inhaler 10 of the present invention wherein, as in all of the following figures unless stated otherwise, references to, for example, the "upper" or "lower" portions of an element will refer to the relative location and orientation of the elements in the Figures.

As represented FIG. 1A, a dry medication inhaler 10 includes a mouthpiece 12 and a body 14 enclosing a medication container 16. In a typical embodiment, mouthpiece 12 and body 14 may have, for example, generally cylindrical or oval external cross sections and the exterior cross section of the upper portion of mouthpiece 12 may be further shaped into, for example, a cross section that can be comfortably received into a patient's mouth.

Referring first to body 14, body 14 generally forms a structure for enclosing a medication container 16 and, as shown in FIG. 1A, typically has a cylindrical main body 14A that includes an axially extending container chamber 14B having a length and diameter sized and shaped to receive and enclose a medication container 16. The body 14 includes one or more air passages 18 for drawing air into and through the medication container 16, which are represented in the figure as including a lower air passage 18A extending downwards from the bottom end of container chamber 14B and intersecting horizontally extending air passages 18B and 18C that connect with the air exterior to body 14 to provide a lower air passage 20 extending between the exterior air and into the bottom end of container chamber 14B. It should be noted, however, that the alternate configurations of lower air passages 18A and 20 may be used. For example, there may be only one air passage 18B or 18C intersecting lower air passage 18A there may be several air passages connecting between the outside air and lower air passage 18A rather than just one or two lower air passages 18B/18C. In yet other embodiments, one of more air passages 18B/18C may intersect lower air passage 18A at a slant or slants, rather than at right angles, or lower air passage 18A may extend in a straight path to connect with the outside air, or lower air passage 18A or one or more air passages 18B/18C may connect with the outside air through a "torturous", curves or zig-zagged path or paths, rather than a straight path or paths. In yet other embodiments the air passage connection between lower air passage 18A and the outside air may take the form of a slot or slots aligned parallel to, perpendicular to or at an angle or angles with lower air passage 18A, and so on.

In the illustrated embodiment, body 14 includes a cylindrical wall 14C that surrounds container chamber 14B and that extends upwards above the upper end of container chamber 14B wherein, in the illustrated embodiment, the upward extension has an exterior diameter that is less than the exterior diameter of the main part of body 14A. As shown, the interior of cylindrical wall 14C forms an upward end of container chamber 14B and, as discussed below, cylindrical wall 14C sealingly mates with a corresponding portion of mouthpiece 12. It should be recognized, however, as will be apparent from FIG. 1A and the following descriptions, that the exterior diameter of cylindrical wall 14C may, for example, be equal to that of main body 14A, with corresponding adaptations to the mating contours of mouthpiece 12.

Referring now to mouthpiece 12, mouthpiece 12 generally provides a mechanism for opening a medication container 16 residing in body 14 and for delivering the medication therein to a user. As illustrated in FIG. 1A, mouthpiece 12 includes two axially connected interior spaces, including a mouthpiece chamber 12A in the upper portion of mouthpiece 12 and a body chamber 12B in the lower portion of mouthpiece 12, with the two chambers being axially connected through a needle passage 12C. As shown, the interior of body chamber 12B and the lower part of needle passage 12C are shaped and sized to receive the upper portion of main body 14A and cylindrical wall 14C, thereby forming an enclosed protective container chamber 14B in which a medication container 16 can reside. The illustrated embodiment of the inhaler 10 may further include a ring seal 22, located in needle passage 12C, that seals against the outer diameter of cylindrical wall 14C to form a single medication passage 24 that extends from lower air passage 20 and through container chamber 14B and any container 16 residing therein and needle passage 12C to mouthpiece chamber 12A. In other embodiments, however, the seal may take the form of a surface to surface contact seal between the corresponding surfaces of main body 14A and mouthpiece 12, or a sealing function may not be required.

As also illustrated in FIG. 1A, mouthpiece 12 includes a hollow medication delivery needle 26 that functions to open the medication container 16, thereby making the medication accessible to the patient or user, and as a delivery mechanism for extracting the medication from the medication container 16 and delivering the medication to the user or patient. As shown, an upper section of medication delivery needle 26 resides in needle passage 12C with the upper end 26U of medication delivery needle being located in the region of the intersection of needle passage 12C and mouthpiece chamber 12A. As will be shown in following discussions of alternate implementations, the upper end of delivery needle 26 may be located over an axial range extending from within needle passage 12C to within mouthpiece chamber. As shown, and as discussed below, the lower end 26L of medication delivery needle 16 extends downwards to pierce medication container 16 and to form a passage for the delivery of the medication when mouthpiece 12 and main body 14 are axially telescoped into the activated position.

Figure 1B:
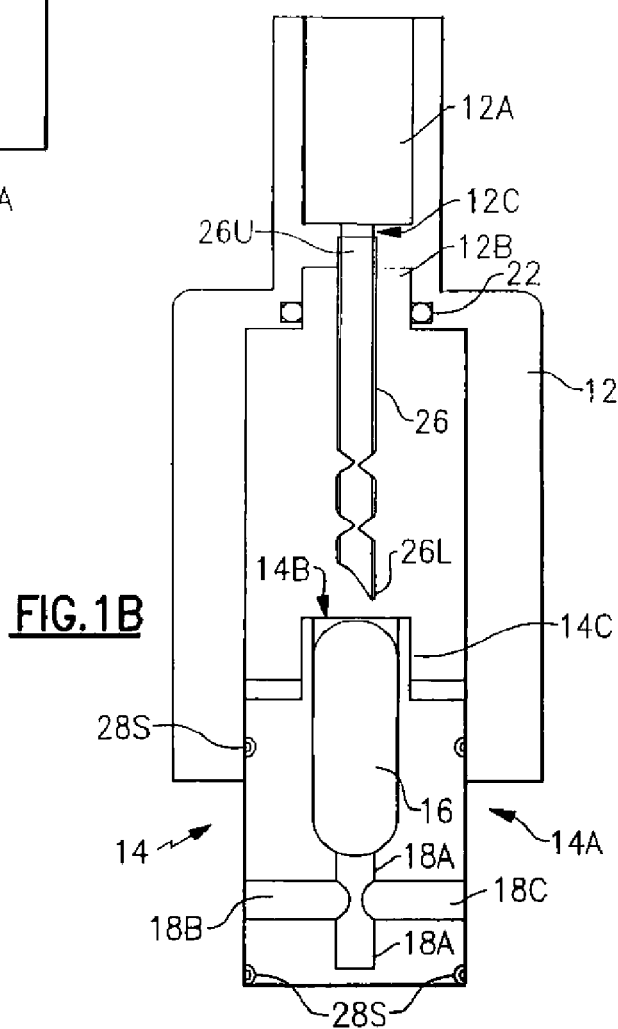
FIGS. 1B and 1C are diagrammatic illustrations of the stored and activated positions of an inhaler.
Figure 1C:
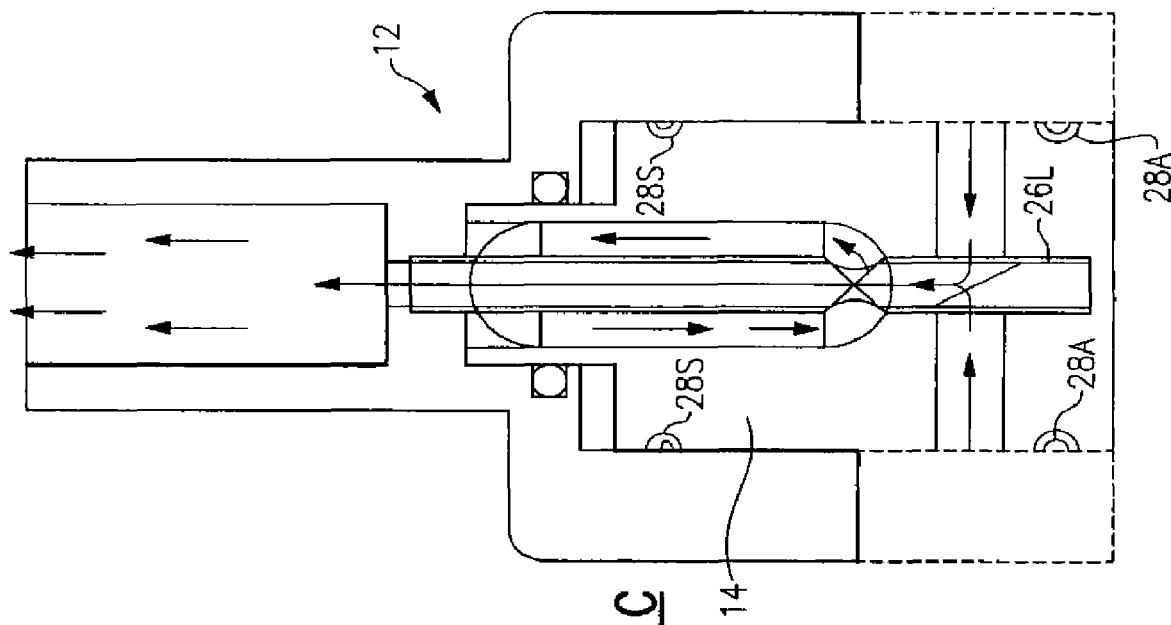

Therefore considering the use and operation of an inhaler 10, and as illustrated in FIGS. 1B and 1C for an embodiment of an inhaler 10, in an initial step a medication container 16 is inserted into container chamber 14B and mouthpiece 12 and main body 14 are fitted together to enclose the medication container 16, whereupon the inhaler 10 may be said to be in the "storage" state, that is, assembled with a medication container 16 but not yet activated to release the medication from the medication container 16.

When mouthpiece 12 is in the "storage" position with respect to main body 14, that is, when mouthpiece 12 is partially but not fully engaged with main body 14 as illustrated in FIG. 1B, the lower end 26L of delivery needle 26 will extend downwards from mouthpiece 12 and along the common axis of mouthpiece 12 and main body 14 to a point short of container chamber 14B and a medication container 16 residing in container chamber 14B.

At this point, the medical personnel administering the medication to a patient or the patient themselves, may activate the inhaler 10 to release and deliver the medication by pushing mouthpiece 12 and main body 14 together to the fully activated position. Once the medication has been administered to the patient, as discussed further below, the inhaler may be opened to remove and discard the expended container and the inhaler subsequently prepared for another use by inserting a new container when needed. The inhaler 10 may thereby be employed as a multi-use device or, if discarded with the expended container after use, as a single use device, depending upon the particular requirements under which the inhaler 10 is employed.

In the alternative, however, the inhaler 10 can remain in the "storage" state for an extended period determined by the packing of the inhaler 10 or the medication container or containers therein, thereby allowing inhalers 10 to be prepared, stored and delivered as pre-loaded ready-to-use devices for the delivery of a particular medication. In this regard, it must be noted that medications are typically enclosed in an "overpack", that is, an additional air-tight packaging, to extend the storage life of the medications, and that the use life of medications once removed from the overpack is often limited to, for example, 30 days. These methods may be applied to pre-loaded inhalers 10 by, for example, enclosing the the pre-loaded inhaler 10 in an overpack or by enclosing the medication containers themselves in individual overpacks within the inhaler 10 whereupon, for example, activation of the inhaler 10 mechanism would open the overpack as well as the container.

It should also be noted in this regard that, as will be described further in a following discussion, mouthpiece 12 may be engaged with main body 14 and retained in the storage position by, for example, corresponding circumferential detent rings and grooves on the matching corresponding interior surfaces of mouthpiece 12 and main body 14, or by any other equivalent detent mechanism 28S. In these implementations, therefore, a positive application of force along the common axis of mouthpiece 12 and main body 14 would be required to overcome the detent so that mouthpiece 12 could move to become fully engaged with main body 14 and a medication container 16 residing in container chamber 14B would remain sealed until such a force was applied.

In this regard, it must be noted that a number of alternative implementations may be employed to allow the storage detect function when the inhaler 10 is to be employed as a pre-loaded ready-to-use devices. For example, FIG. 1B illustrates an embodiment wherein the portion of mouthpiece 12 that encloses main body 14A when the inhaler 10 is in the "storage" configuration is extended so that the detent mechanism 28S located at the lower part of mouthpiece 12 engages an upper portion of main body 14 in such a manner that medication delivery needle 26 is held in a "storage" position short of contacting the container 16. In other embodiments, however, the necessary clearance between the medication delivery needle 26 and the container 16 may be achieved, for example, by a cylindrical body enclosing either or both of mouthpiece 12 and main body 14A and having a detent mechanism or mechanisms interacting with mouthpiece 12 and main body 14A.

Therefore next considering the activation and activated state of an inhaler 10, as illustrated in FIG. 1C, the application of a sufficient axial force to mouthpiece 12 and main body 14 will cause mouthpiece 12 and main body 14 to move towards one another and into the fully activated position. This motion will result in delivery needle 26 being forced downwards through container chamber 14B and a medication container 16 residing therein until delivery needle 26 extends through container chamber 14B and the medication container 16 and into lower air passage 18A until lower end 26L of delivery needle 26 is located in lower air passage 18A at a point lower than horizontally extending air passages 18B and 18C.

The inhaler 10 is then In the fully activated, or engaged, position of the inhaler 10, wherein medication container 16 has been opened, or unsealed, to provide access to the medication therein and an air passage has been formed that extends from air passage 20 and through the medication container 16, container chamber 14B and needle passage 12C and into mouthpiece chamber 12A.

At this point, it should be noted that mouthpiece 12 and main body 14 may include additional corresponding circumferential detent rings and grooves on their matching corresponding interior surfaces, or equivalent latching detent mechanisms 28A, to prevent the separation of mouthpiece 12 and main body 14 after the inhaler 10 has been activated. This feature would prevent the refilling and re-use of the inhaler, so that the inhaler 10 would be a single use, throw-away device, which would be particularly useful with relatively untrained or uneducated medical personnel or patients.

Figure 2A:
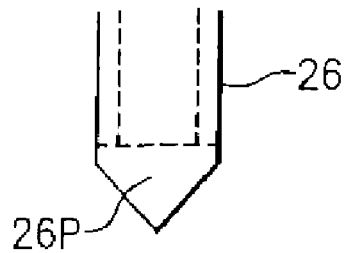
FIGS. 2A-2F are diagrammatic illustrations of possible implementations of a medication delivery needle.
Figure 2B:
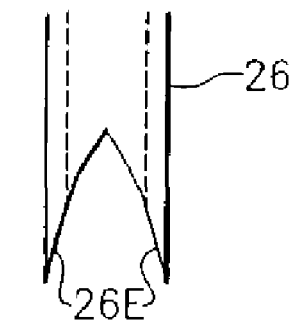
Figure 2C:
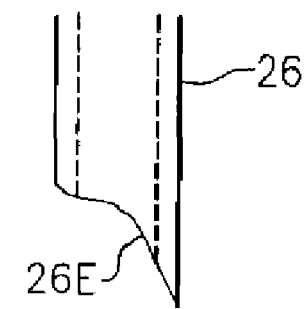
Figure 4:
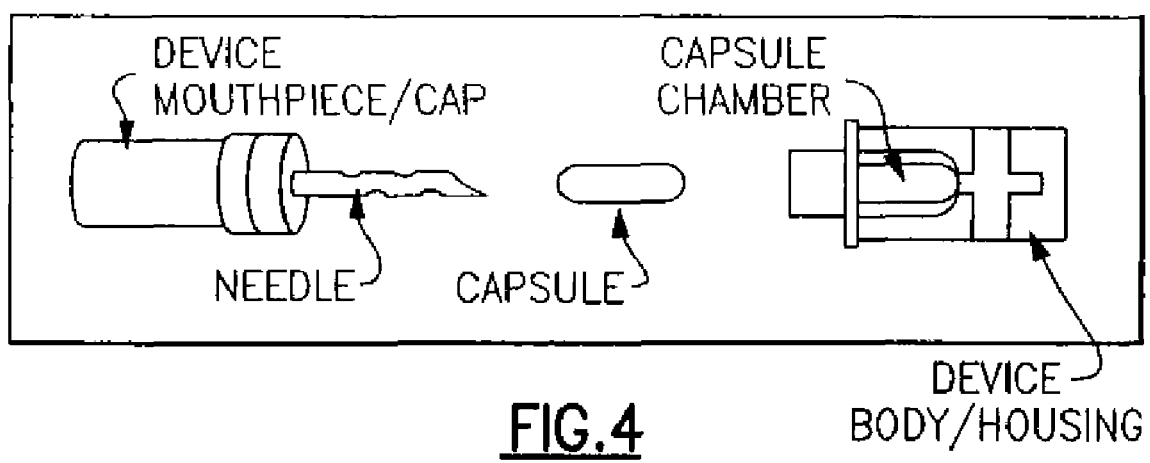
FIG. 4 is a disassembled view of an inhaler.
Figure 3A:
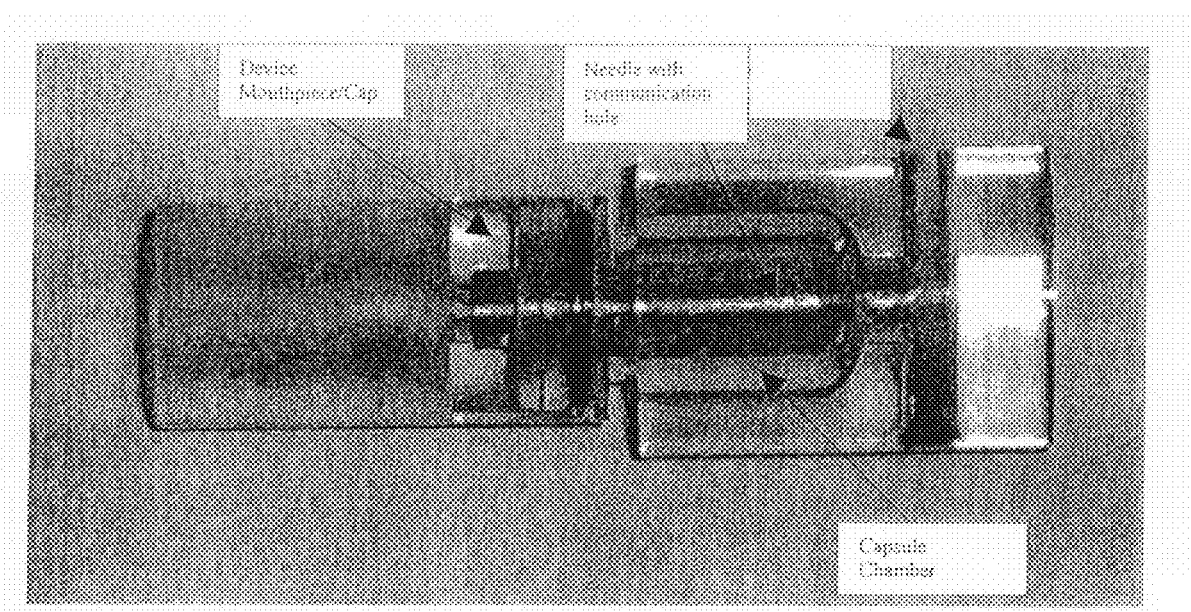
Figure 3B:
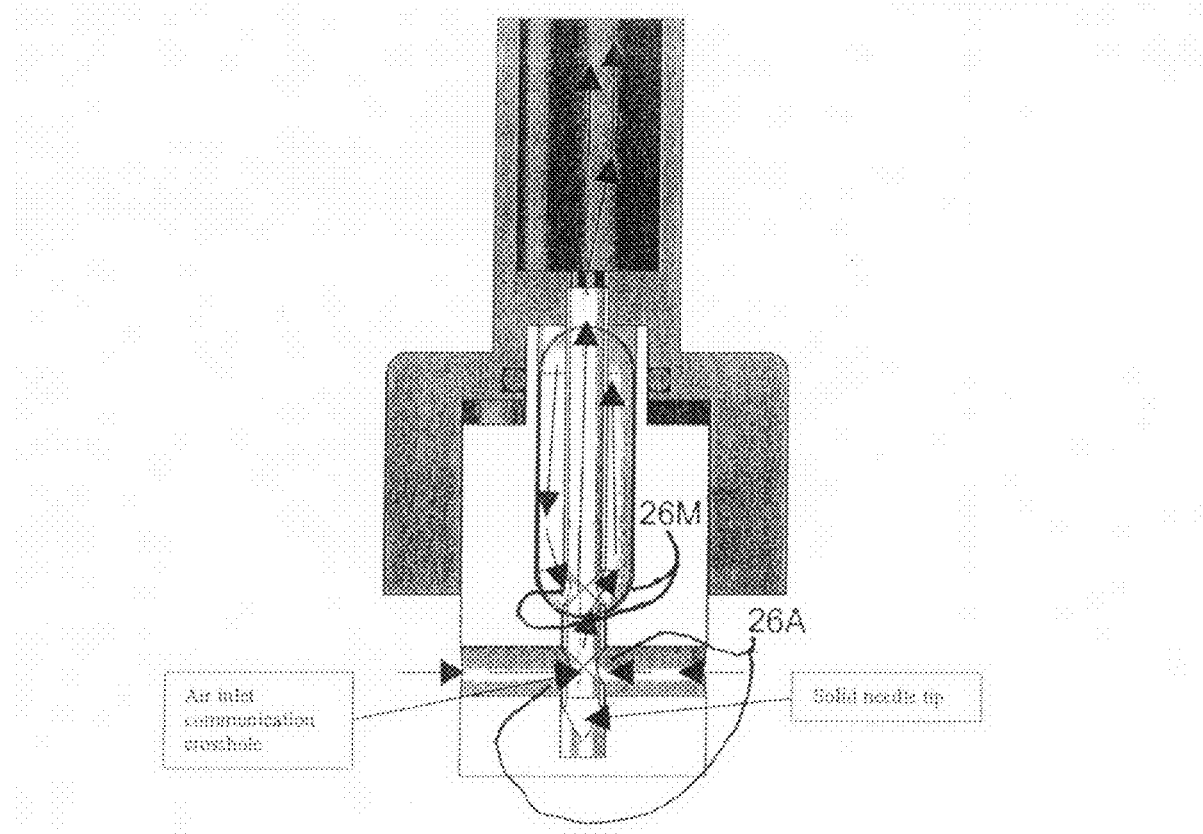

The operation of an inhaler 10 and the delivery needle 26 in delivering medication to the patient is illustrated in FIGS. 2A-2D, illustrate alternate embodiments of a delivery needle 26 and, in conjunction with FIGS. 1A-1C, the delivery of medication from a medication container 16 to a user. As shown in FIGS. 2A-2C, lower end 26L of a delivery needle 26 is shaped to facilitate the penetration of the delivery needle 26 into and through a medication container 16 residing in the container space 14B. For example, lower end 26L may be closed with a sharp, penetrating point 26P or may be shaped into single or double slanting edge 26E terminating in sharp points.

Figure 2F:
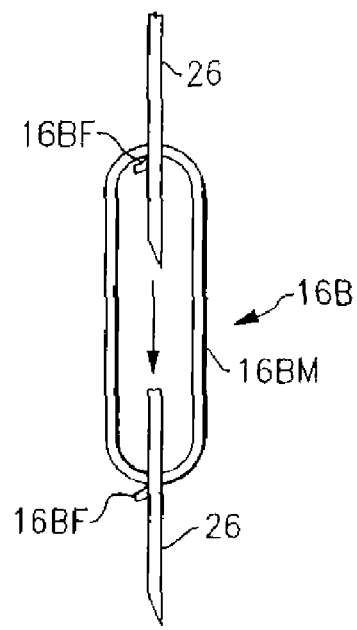
Figure 2D:
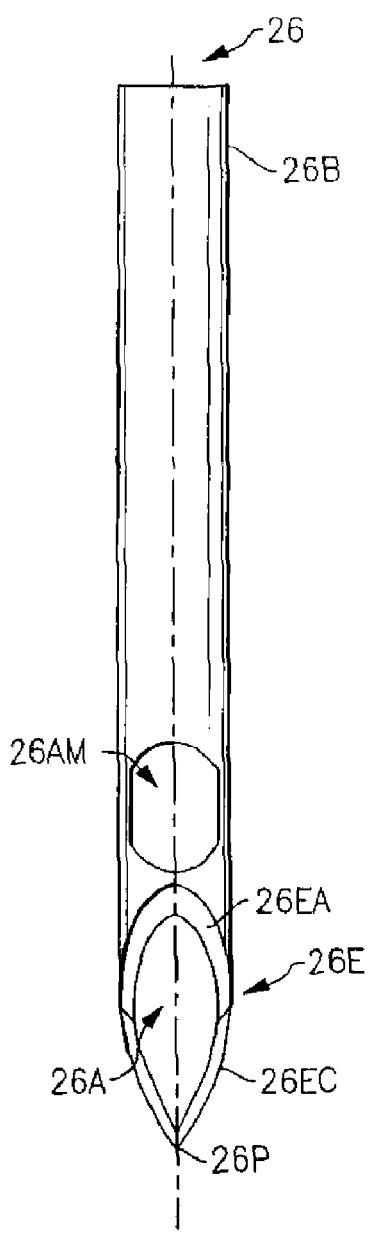
Figure 2E:
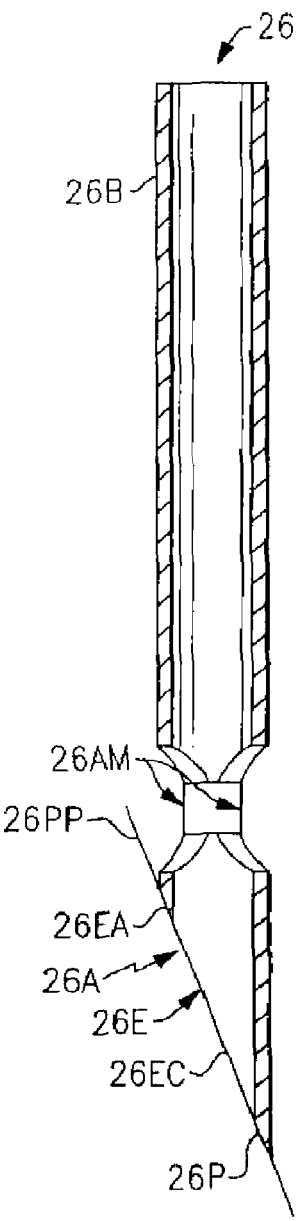

FIGS. 2D and 2E, in turn, illustrates a design of a delivery needle 26 that is particularly adapted to avoid the production of particles or dust of the container material during puncture or destruction of the container to gain access to the medication therein and FIG. 2F illustrates the operation of the delivery needle 26 on a medication container 16. As illustrated in FIG. 2D, the delivery needle 26 is comprised of a hollow generally cylindrical body 26B terminating in a puncture point 26P formed at the extreme end of body 26B by a puncture plane 26PP that extends obliquely, that is, at a slant, across the diameter of body 26B at an angle of, for example, approximately 30° to the axis of body 26B. As shown, puncture plane 26PP forms a generally oval or elliptically shaped opening into the interior of the needle wherein the edge or rim of the opening is defined by puncture edges 26E that extend along the intersections between body 26B and puncture plane 26PP from puncture point 26P to a generally diametrically opposite point on body 26B that is located along body 26B at a distance away from puncture point 26P that is compatible with the angle of puncture plane 26PP and the diameter of body 26B.

As indicated in FIGS. 2D and 2E, puncture edges 26E are formed of cutting edges 26EC that extend from puncture point 26P and back along both sides of puncture edge 26E for a selected distance, such as approximately one half the length of puncture edges 26E. Puncture edges 26E are then continued by anti-coring edges 26EA that extend along puncture edges 26E from the back end of cutting edges 26EC to the rearmost point of puncture edge 26E, where puncture edges 26E rejoin at the outer surface of body 26B.

In use, and referring to FIGS. 2D, 2E and 2F, puncture point 26P establishes an initial opening or puncture into the material 16BM of the medication container 16 and cutting edges 26EC follow puncture point 26P into material 16BM with a cutting action to begin separation of a flap 16BF from the material 16BM. The separation of flap 16BF from material 16BM will continue as delivery needle 26 continues to penetrate the material 16BM of the medication container 16, and will continue until anti-coring edges 26EA come into contact with the material 16BM. At this point, delivery needle 26 will have cut out a flap 16BF that will form an opening or hole through the material 16BM of the container 16 wall wherein the opening or hole will be of approximately the diameter of body 16B and will occupy approximately one half to two thirds of the circumference of body 16B and wherein the flap 16BF is attached to the material 16BM of the wall of the container 16.

According to the present invention, anti-coring edges 26EA are formed to have a non-cutting shape, such as a radius rather than a cutting edge, by, for example, grit blasting or polishing or swaging of the anti-coring edges 26EA. As such, the cutting of flap 16BF from the material 16BM of the wall of the container 16 will cease when anti-coring edges 26EA enter the material 16BM of the container 16. Continued penetration of delivery needle 26 into container 16 will thereby result in the flap 16BF and the material 16BM being pushed aside or otherwise distorted by anti-coring edges 26EQ to finish forming the passage through the wall of the container 16 while leaving the flap 16BF attached to the wall of the container 16.

The above described penetration of the wall of the container 16 and the forming of a hole or passage with an attached flap 16BF will be repeated when the delivery needle 26 reaches and penetrates the opposite wall of the container 16, but with the flap 16BF being formed on the outer side of the container 16 wall rather than on the inner side of the container.

Continuing with alternate embodiments of a delivery needle 26 as illustrated in FIGS. 2A-2C, it will be apparent from the illustrated examples of alternate embodiments that the basic geometry of the above discussed needle 26, and in particular the configuration of the puncture point or points and various edges, may be configured in a number of ways. It must also be noted that each delivery needle 26 will include at least one air inlet 26A opening into a corresponding one of air passages 18B and 18C, thereby allowing a passage of exterior air into the interior of hollow delivery needle 26 and up needle 26 towards the medication container 16 and, eventually, mouthpiece chamber 12A and the user.

Each delivery needle 26 will further include at least one medication inlet 26M in the region of and opening into the interior of the medication container 16 to allow the medication contained in the medication container 16 to be drawn into the interior of the delivery needle 26 and up the interior of the delivery needle 26, together with the exterior air from air inlets 24A, and into the mouthpiece chamber 12A and to the user.

In the instance of a medication delivery needle 26 as illustrated in FIGS. 2A-2C, the opening formed by puncture plane 26PP cutting across the diameter of the medication delivery needle 26 to form the puncture point 26P, the puncture plane 26PP, the puncture edges 26E, the cutting edges 26EC and the anti-coring edges 26EA will comprised an air inlet 26A. A medication delivery needle 26 as illustrated in FIGS. 2A-2C will also include one or more air/medication ports 26AM in the length of the medication delivery needle 26 above puncture plane 26PP. As will be described further in the following air/medication ports 26AM may extend on both the inner and the outer sides of the lower opening of the punctured medication container 16, so that each air/medication port 26AM will serve both as a air inlet 26A and a medication inlet 26M.

Figure 3B:
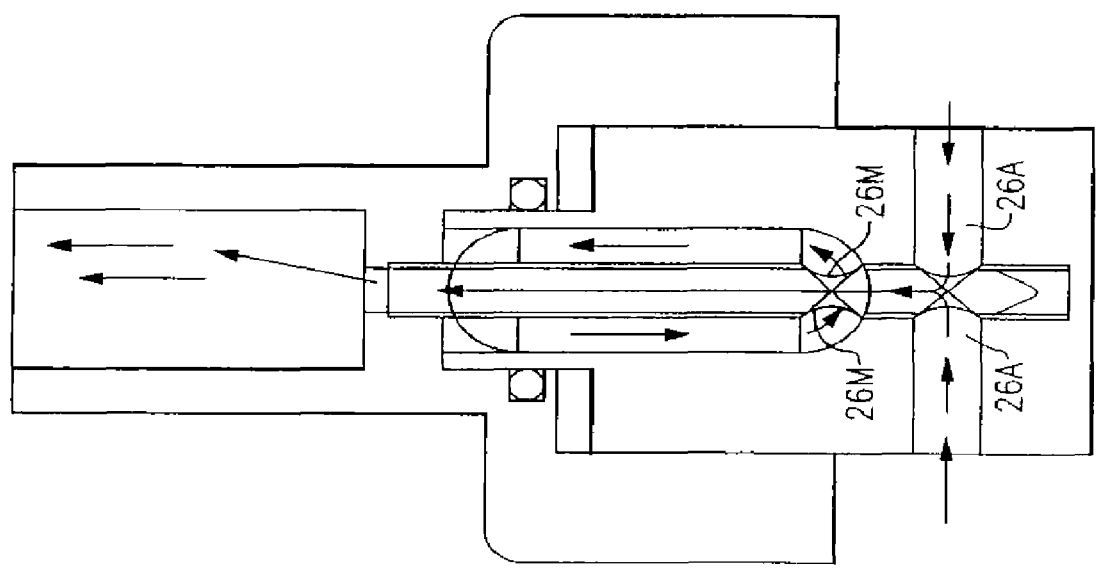
FIGS. 3A-3D are diagrammatic representations of alternate embodiments of a dry medication inhaler.
Figure 3D:
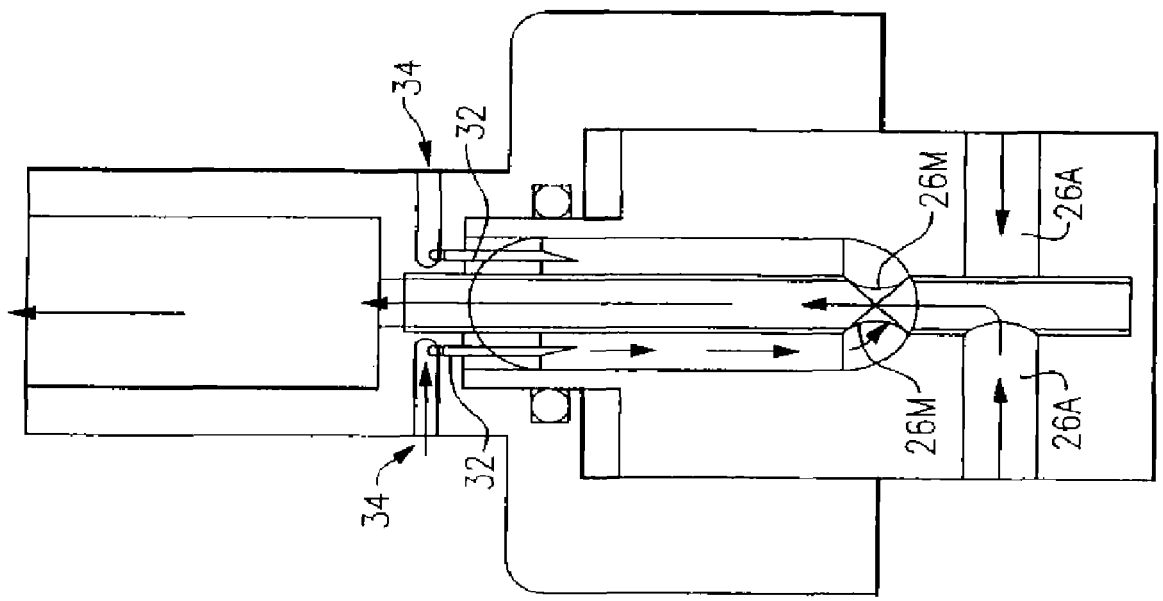
Figure 3C:
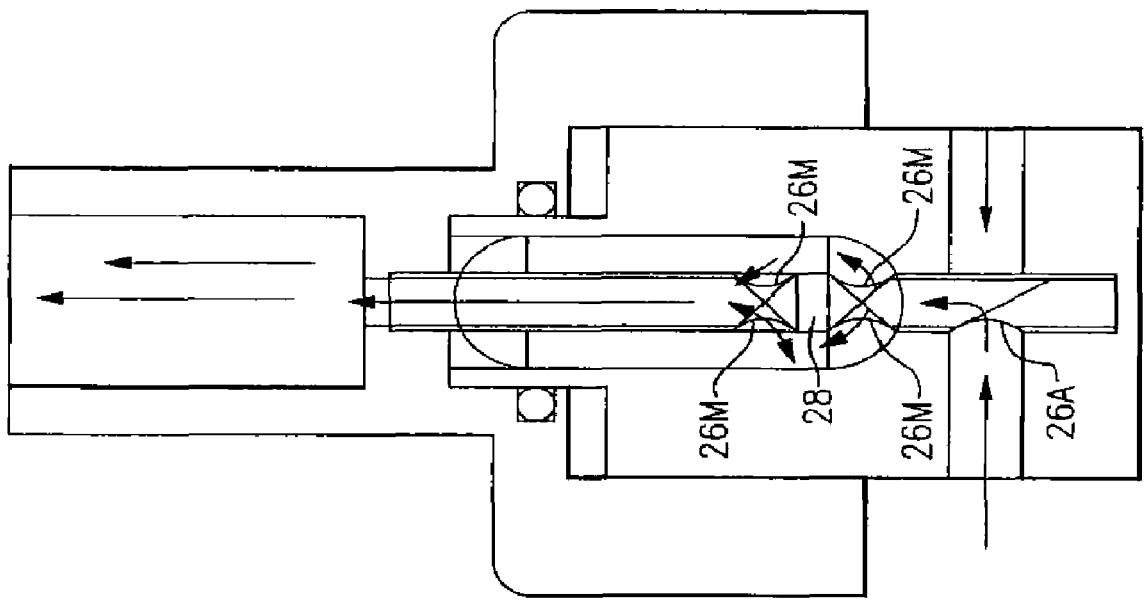

Referring now to FIGS. 3A-3D, FIG. 3A is a view of an assembled inhaler 10 and FIGS. 3B-3D are diagrammatic representations of alternate embodiments of an inhaler 10. FIG. 3B, for example, illustrates an inhaler 10 wherein the delivery needle 26 is provided with a penetrating point 26.

FIG. 3C shows a delivery needle 26 having two vertically spaced pairs of medication ports 26M separated by a baffle 30 closing the interior bore of the delivery needle 16 between the upper and lower pairs of medication inlets 26M. This design prevents clogging and clumping of the medication within the medication container 16 by forcing air drawn from air passage 20 and into the lower part of the delivery needle 26 to vent into the medication container 16, thereby increasing the efficiency of "scouring" of the medication from the container 16 by providing a greater pressure differential through the container 16 and thus a greater volume of air flow. Depending upon the type and composition of medication in the container 16, this design may also provide a "stirring" of the medication therein before carrying the medication out of the container 16 through the upper pair of medication ports 26M and up through the needle 26 to the mouthpiece chamber 12A, thereby reducing the possibility of "clogging" or trapping of the medication in the container 16 or the flow passages.

FIG. 3D in turn illustrates an embodiment of an inhaler 10 that addresses the same approaches as the embodiment of FIG. 3C, but in a different form. In the embodiment of FIG. 3D, and in addition to medication needle 26, which may include one or more air/medication ports 26AM, the lower part of mouthpiece 12 that abuts main body 14 and, in particular, container chamber 14C, supports one or more hollow secondary needles 32 that connect with the exterior air through corresponding secondary air passages 34 and that extend into container chamber 16. When mouthpiece 12 and main body 14 are moved into the activated position, secondary needles 32 will penetrate the medication container 16 so that air will be drawn through air passages 32 and secondary needles 34 and into the upper part of the medication container 16 when the user draws on mouthpiece 12. The resulting flow of air into the upper part of the medication container 16 and downwards and out through medication inlets 26M will assist in preventing clogging and clumping of the medication and will assist in carrying the medication out of the medication container 16 and up needle 26 to mouthpiece chamber 12A. It will be understood by those of ordinary skill in the relevant arts that the diameters of secondary needles 32 and needle 26 and of the various air and medication ports and passages must be selected in consideration of the suction that can be comfortable exerted on mouthpiece 12 by a patient, the air flow necessary to move the medication to the patient, and the desired rates and proportions of air and medication flows through the inhaler 10

It will be understood that the inhaler 10 of the present invention, including the mouthpiece 12, the main body 14A and the medication delivery needle 26, may be constructed of any of a range of materials suitable to their intended purposes, such as glass, metal, plastics or ceramics. It will also be understood that the term "container" used in the above descriptions, such as the medication container 16, is used in the generic and general meaning as a container for medication, rather than in a specific and limiting sense. It will be apparent from the above discussions that a "container" as the term is used herein and in the claims may assume any of a variety of shapes other than the generally oval capsule shown herein for illustrative purposes, such as a blister pack, and that the container may be made of any of a wide range of materials. It must also be understood that the specific shapes, proportions and dimensions of the various elements of an inhaler 10 will be at least in part dependent upon the constitution of the medications to be dispensed. In the case of dry medications, for example, some medications are comprised of pure medication, often comprised of "snowflake"-like particles, while others are comprised of particles of medication attached to particles of a carrier material, all of which may effect the materials and dimensions of a specific design of an inhaler 10.

Figure 5:
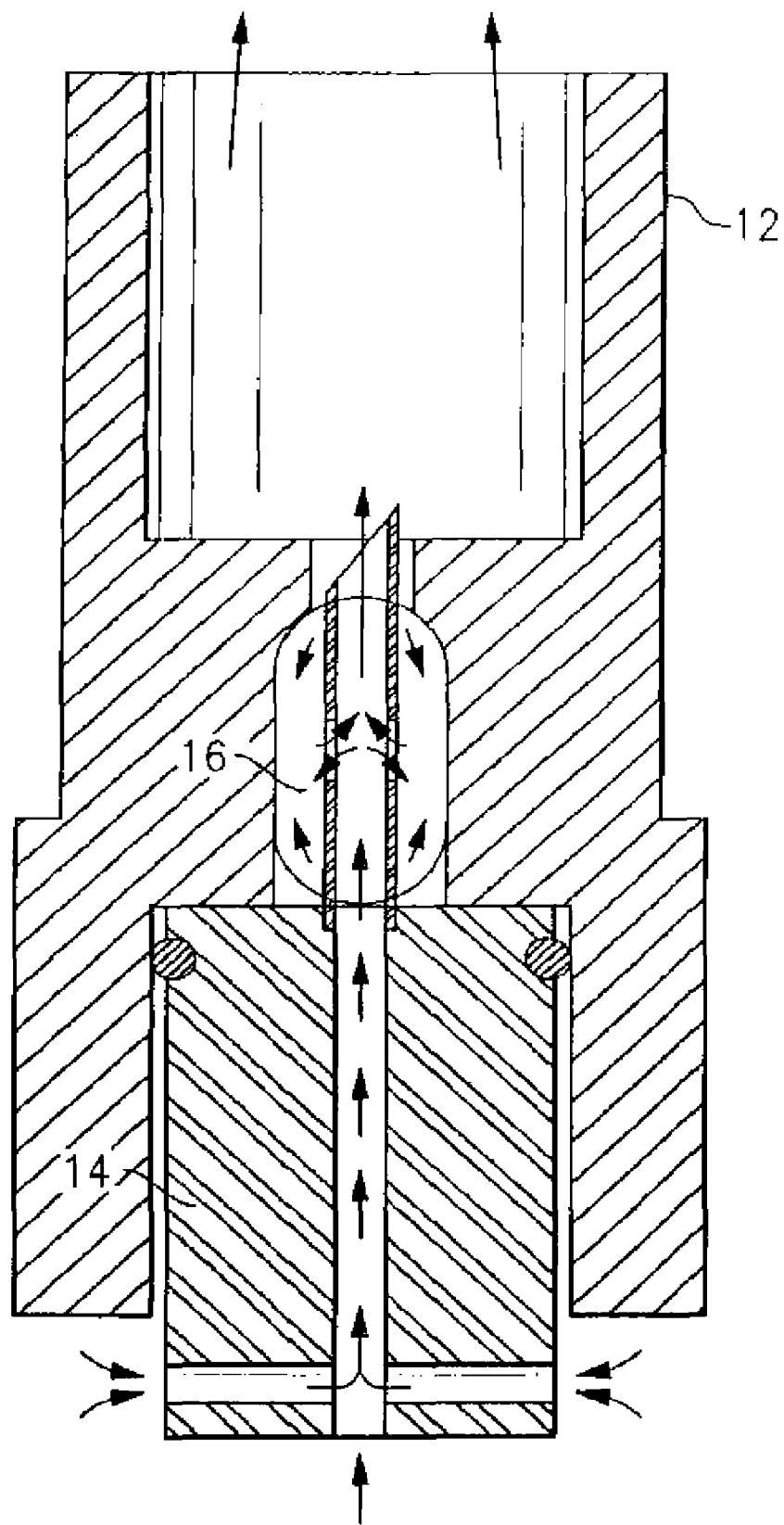
FIG. 5 is a diagrammatic representation of an alternate embodiment of a dry medication inhaler in which the roles of the mouthpiece and body are reversed with respect to the location and operation of the medication delivery needle.

In further examples, of alternate embodiments or features, the delivery needle 26 may extend into mouthpiece chamber 12A, or the entry of needle passage 12C may be surrounded by a cylindrical baffle, to direct the flow of air and medication from needle passage 12C towards the mouthpiece outlet to the user, thereby assisting in preventing clumping and clogging and the deposition of the medication on the inner surfaces of the mouthpiece chamber 12A. The circumference of the lower part of mouthpiece chamber 12A may also include additional air inlets for the same purpose, that is, the creation of air currents to direct the mixture of air and medication as desired. Yet another alternate embodiment is illustrated in FIG. 5, which is a diagrammatic representation of an alternate embodiment of a dry medication inhaler in which the roles of the mouthpiece and body are reversed with respect to the location and operation of the medication delivery needle.

It should also be noted that while an inhaler 10 of the present invention is intended for use with dry medications in the presently preferred implementations, it is possible to use the inhaler of the present invention with, for example, a "dry" medication comprised of a "wet" medication retained in the container in, for example, an air gel or other absorbent or micro-pore material, or semi-solid medications, either of which would be delivered by evaporation or sublimation into the air flowing through the container. In this sense, therefore, the term "dry" medication includes medications that are "wet" but not liquid in the sense of a substance that will flow readily.

In still further examples of possible implementations of the present invention, an inhaler 10 has been described herein above as a single-container single-use device, as a single-container multi-use device, and as a pre-loaded ready-to-use device. In yet other embodiments the inhaler 10 may be implemented as a "multi-shot" device wherein, for example, main body 14 is provided with multiple container chambers 14B that can be selected by, for example, rotating or sliding the main body 14A, or with a single container chamber 14B and a rotary or sliding magazine for loading successive containers 16 into the container chamber 14B.

B. Alternate Embodiments

Effects of Container Size

As described briefly above, medication containers 16 may differ significantly in size, that is, length, width and capacity, as well as shape and in the materials from which they are manufactured. Examples of the dimensions of typical capsules are illustrated in FIG. 6C.

Figure 6A:
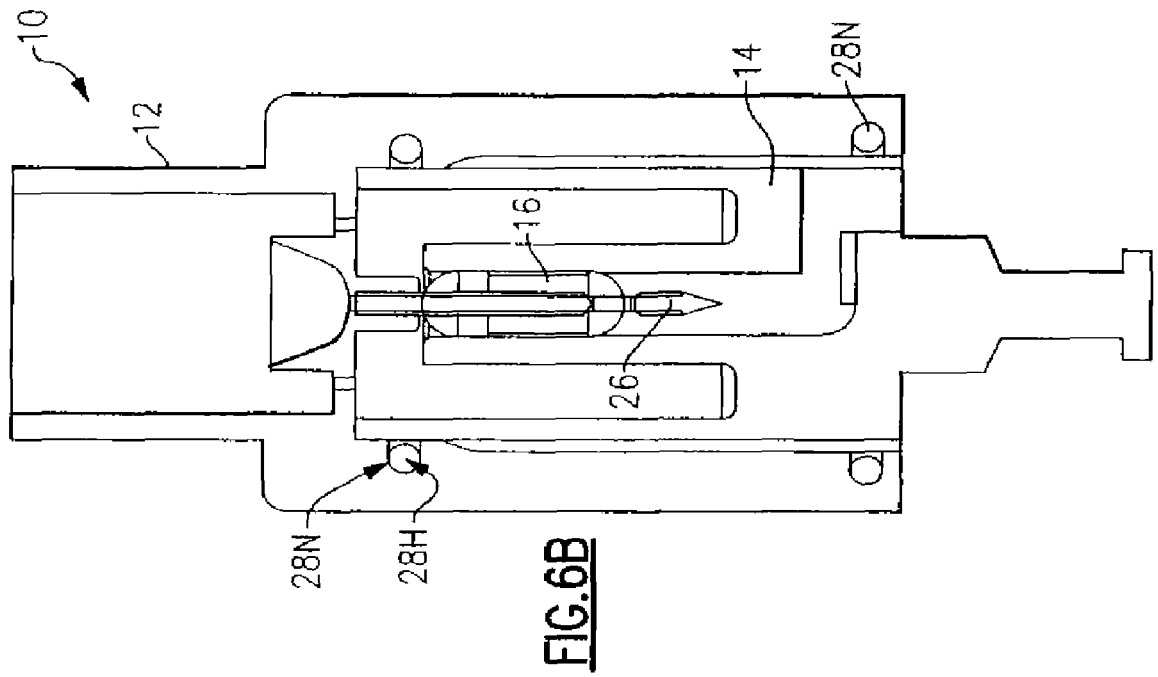
FIGS. 6A and 6B illustrate adaptations of the inhaler for various sizes of medication containers.
Figure 6B:
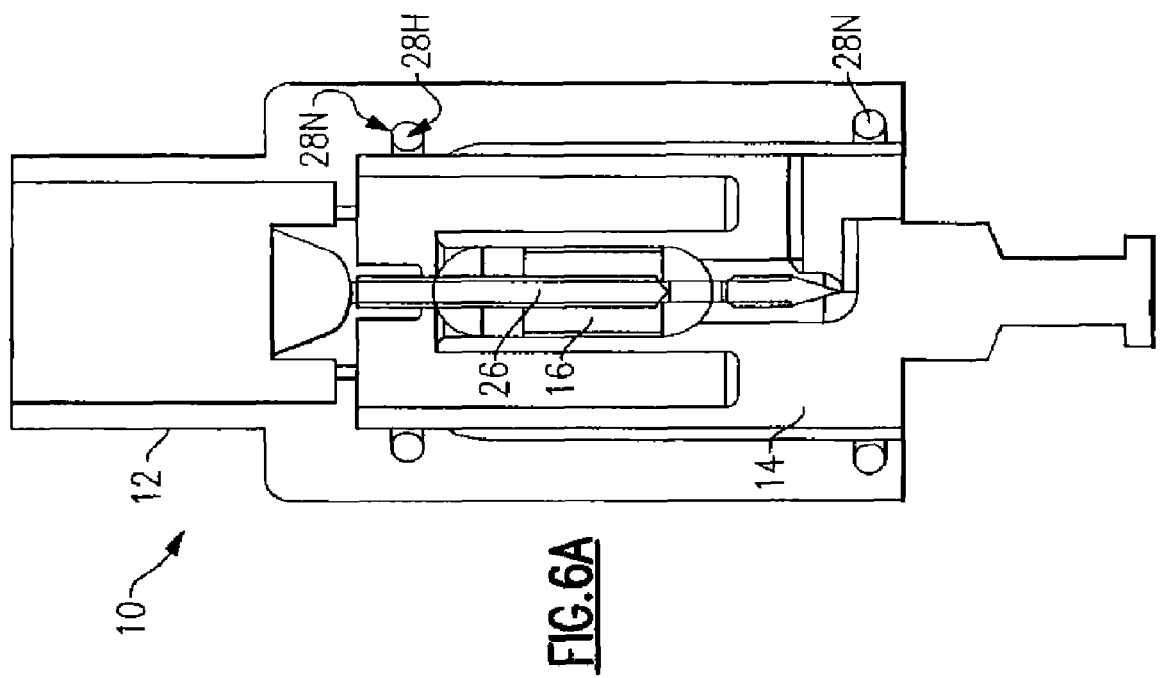
Figure 6C:
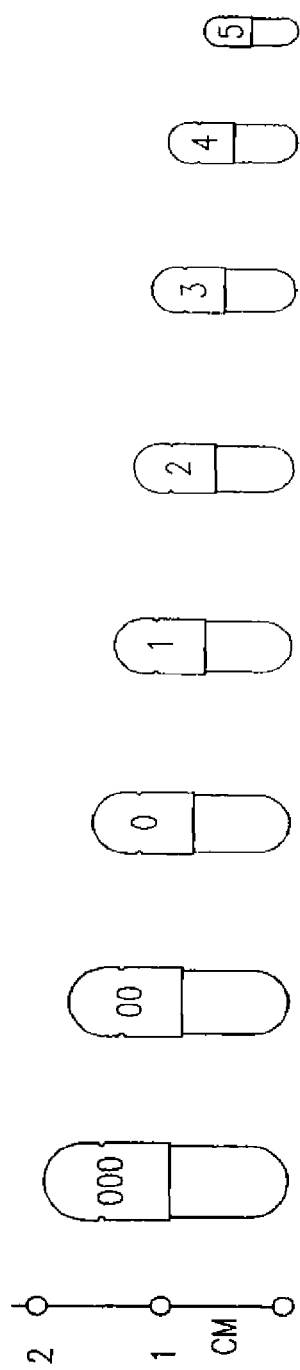
FIG. 6C is a table illustrating capsules of various sizes and capacities.

That is, and as illustrated in FIGS. 6A and 6B wherein FIG. 6A illustrates a larger capacity capsule and FIG. 6B a smaller capacity capsule, the adaptation of a dry inhaler 10 of the present invention to containers of different capacities, dimensions and shapes often requires only changes in the internal dimensions of container chamber 14C and a possible change in the diameter of delivery needle 26 so that the diameter of delivery needle 26 is compatible with the diameter of the medication container 16. The external configuration and dimensions of the dry inhaler 10, however, may remain the same for a wide range of embodiments for different container capacities, dimensions and shapes, examples of which are illustrated in FIG. 6C. It should be noted, however, that the external configuration or dimensions of a given embodiment of an inhaler 10 or a portion thereof could be varied to provide, for example, a visual or tactile differentiation between inhalers 10 loaded with different medications or dosages or with medication containers other than capsules.

In this regard, it must be recognized and understood that while the inhaler 10 of the present invention is generally illustrated and described herein in terms of medication containers 16 in the form of gelatin capsules, that other forms of medication containers 16 may be used readily and with equal facility in an inhaler 10 of the present invention. For example, medication containers 16 may be comprised of blister type packages or other forms of molded containers or that, for example, the medication could be formed into a frangible container or pellet, so that the medication effectively forms its own container. In this instance, for example, the container chamber 14B would effectively form the outer encapsulation of the medication container and would retain the medication in both its sold form and in its powdered form after it had been crushed or pierced by the needle.

C. Alternate Embodiments

Needle Configurations

It will be understood, as discussed above, that the dimensions and configuration or shape of a least certain of the inhaler 10 components, such as the diameter and lengths of mouthpiece 12, body 14, container chamber 14B and medication delivery needle 26 will be dictated largely by the dimensions of the containers 16 and the requirements to transport the medications from the container to the patent. It will be apparent that other factors dictating or influencing the dimensions and configurations of the inhaler 10 components and assembly will include, for example, the requirements of a patient other person in loading and using the inhaler 10 and possible adaptations of the inhaler 10 components and assembly, for example, the automated manufacture and assembly of the components, including the assembly and loading of pre-loaded inhalers 10.

In this regard, it must be understood that the shape, configuration and dimensions of medication delivery needle 26 will have a significant effect on such factors as how the needle 26 penetrates and opens a medication container 16 and how the medication therein is transported from the container 16 to the patient by the air flow through the container 16 and needle 26. For these reasons, therefore, the following will discuss various embodiments and variations in medication delivery needle 26 and other related aspects of an inhaler 10.

Referring first to FIGS. 7A-7D, therein are shown diagrammatic illustrations of an embodiment of a dry inhaler 10 of the present invention and an implementation of medication delivery needle 26 as employed therein. It will be seen from FIGS. 7A-7D that the component parts, configuration and structure of the inhaler 10 represented therein correspond generally to those discussed herein above with regard, for example, to FIGS. 1A-1C, 3A-3C, 4 and 5, and that the shape, configuration and operation of medication delivery needle 26 correspond generally to the medication delivery needle 26 described, for example, in FIGS. 2D-2E.

Figure 7A:
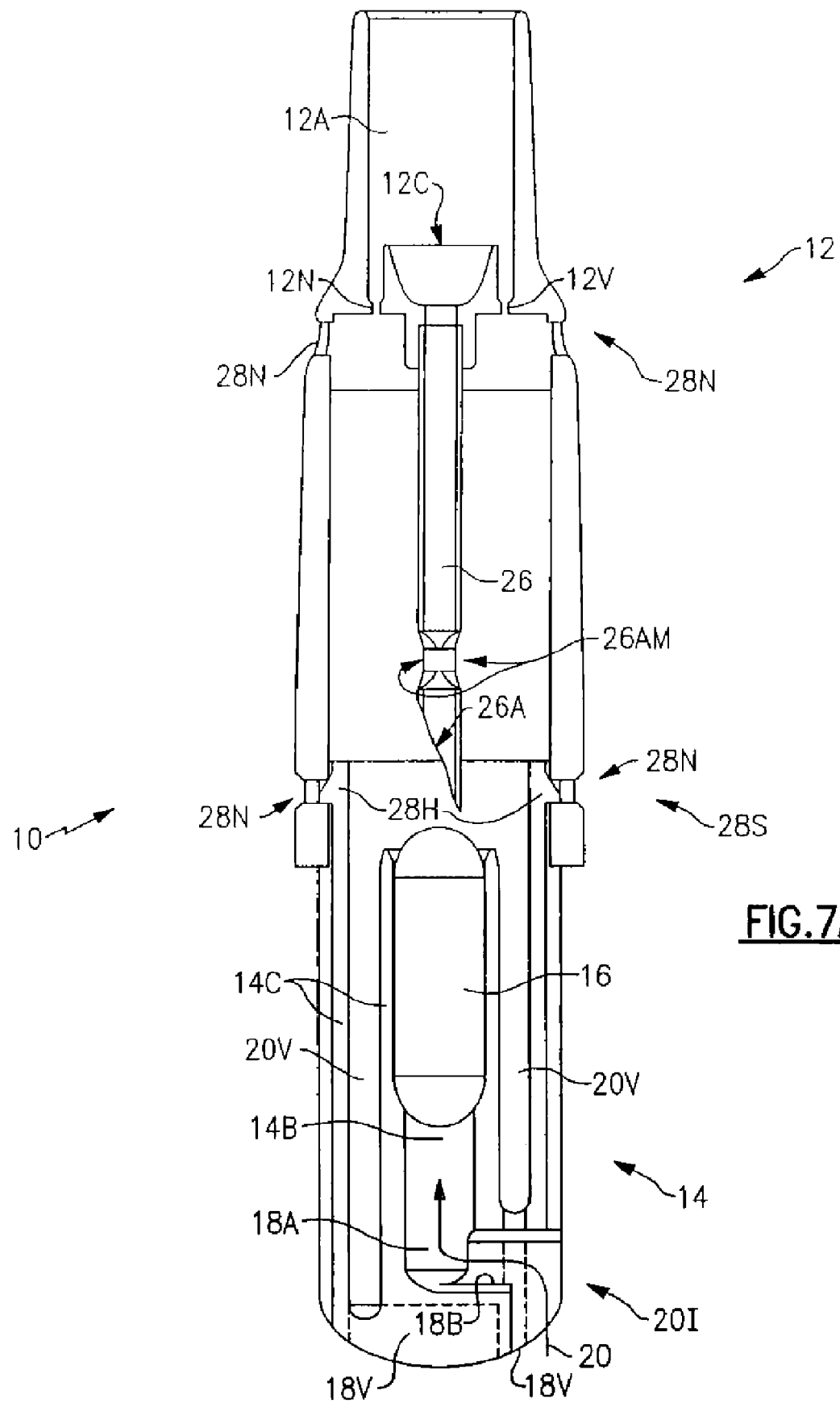
Figure 7B:
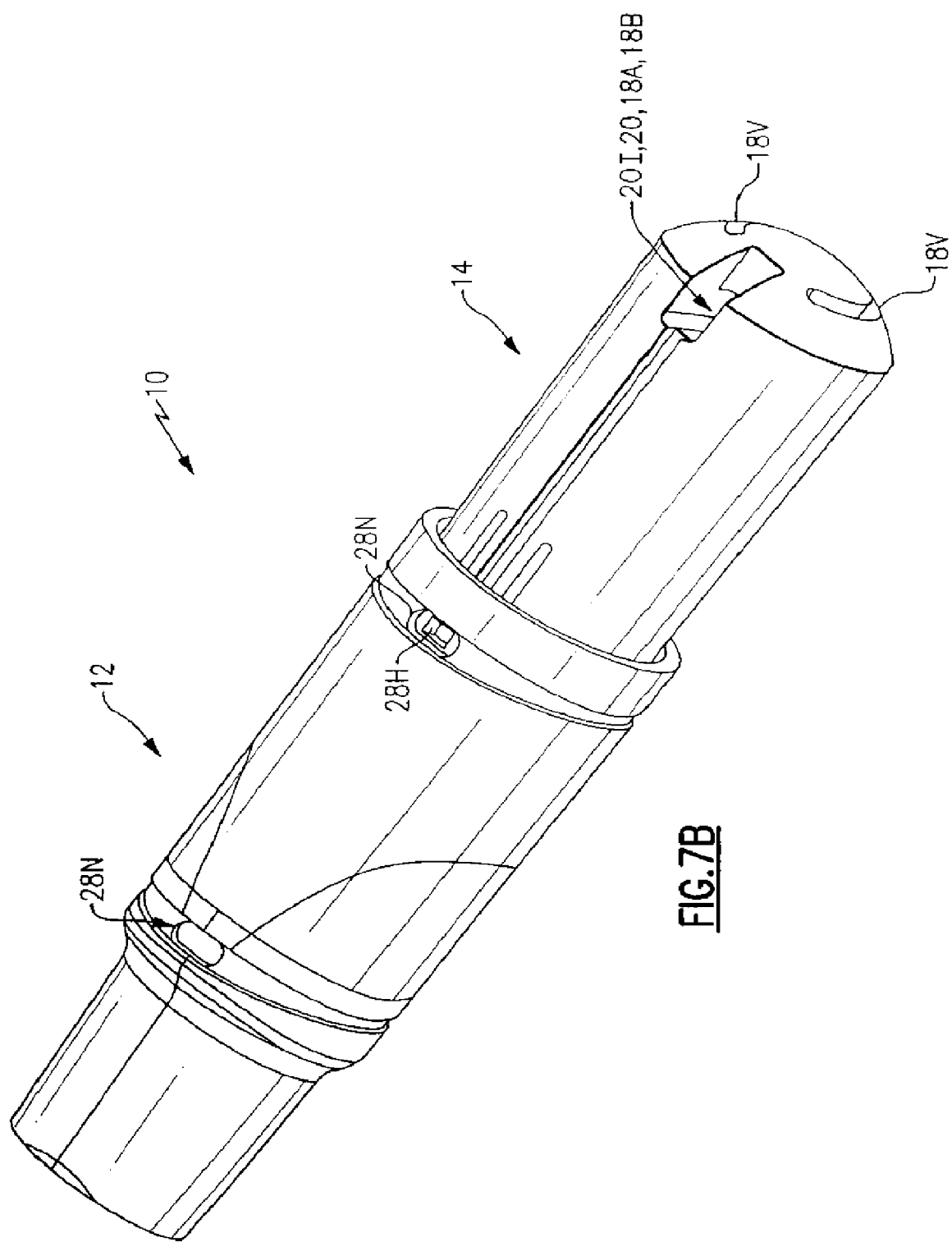

In a typical implementation such as illustrated in FIGS. 7A-7D and, for example, needle 26 is approximately 1 inch long and 0.11 inch in diameter with an inner bore diameter of approximately 0.08 to 0.09 inch. There are two air/medication ports 26AM located on diametrically opposite sides of the needle 26 and each air/medication port 26AM is approximately 0.15 inch long. It will also be noted that when the illustrated inhaler 10 is in the actuated state, that is, mouthpiece 12 and body 14 are pushed together as far as possible and needle 26 has penetrated the container 16 to the maximum extent, as discussed above, the air/medication ports 26AM are positioned such that a part of their length is within the container 16 and a part extends outside the container 16. As discussed, air/medication ports 26AM thereby function as both air inlets 26A and medication inlets 26M and the configuration is such as to provide the optimum air flow rate and circulation pattern to carry the medication from the container 16 into the needle 26 and to the patient through needle 26 and mouthpiece 12, as illustrated in FIG. 7A.

It will also be noted that the length of needle 26, and the length of container chamber 14B, are selected so that puncture point 26P does not contact the lower end of container chamber 14B and so that the lower inner side of mouthpiece 12, through which needle 26 passes, does not contact and inadvertently crush the container 16.

In addition, it must be noted that the opening formed by puncture plane 26PP cutting across the diameter of the medication delivery needle 26 to form the puncture point 26P, the puncture plane 26PP, the puncture edges 26E, the cutting edges 26EC and the anti-coring edges 26EA will comprise an air inlet 26A that, like the lower portion of the air/medication ports 26AM, communicate with lower air passage 20 to receive exterior air. Lastly in this regard, should be noted that in this implementation lower air passage 20, connecting air/medication port 26AM and the air inlet 26A to the exterior art, is comprised of a single vertical air passage 18A and a single horizontal air passage 18B connecting with a slot-like air inlet opening 201.

In addition, body 14 includes one or more vent passages 20V concentrically located in cylindrical wall 14C between between container chamber 14B and the outer surface of body 14 and having, in the present embodiment, arc-shaped cross sections. In the illustrated embodiment the lower ends of vent passages 20V connect with the exterior air through a single vent slot 18V while the upper ends of vent passages 20V connect with mouthpiece chamber 12A through vent ports 12V and vent passages 10V. It should be noted that vent slots 18V and 10V are illustrated in this example as being arc-shaped, but it would be recognized that any appropriate shape may be used. Vent passages 20V assist in the extraction of medication from container 16 and through needle 26 and mouthpiece 12 by increasing the airflow through mouthpiece 12 to, in turn, create a suction effect to draw increase air through the container 16 and needle 26.

Referring next to FIGS. 8A-8D, therein are illustrated an alternate embodiment of a medication delivery needle 26, designated as a pyramidal point medication delivery needle 36. As shown, a pyramidal delivery needle 36 is comprised of a hollow tubular body 36B having a lower end terminated and closed by a pyramidal puncture point 36P and at least one air/medication port 36AM. As shown in FIG. 8B, air/medication port or ports 36AM are located along the body 36B or needle 36 so that when the illustrated inhaler 10 is in the actuated state, that is, mouthpiece 12 and body 14 are pushed together so that needle 36 has penetrated the container 16 to the maximum extent, air/medication port or ports 36AM are located partly within the container 16 and partly within and correcting to lower air passage 20. For example, when the inhaler 10 is fully actuated the port or ports 36AM may be located with approximately 9/10ths of the port or ports within the container 16 and approximately 1/10th communicating with lower air passage 20. It will, therefore, be apparent that in a pyramidal needle 36 pyramidal puncture port 36P closes the end of tubular body 36B so that the needle 36 does not include an air inlet 26A at the lower end of the needle 36 and so that the air/medication port or ports 36AM of the needle 36 function as both air inlets 26A and medication inlets 26M of the needle 36 in a manner analogous to air/medication ports 26AM of needle 26.

As illustrated in FIGS. 8A-8D, pyramidal puncture point 36P may assume the form of, for example, a three or four sided pyramid with the tip of the pyramid, which forms the point puncturing the container 16 when the inhaler 10 is actuated, being located on the centerline of the needle 36 and thereby on the centerline of the container 16. Comparison with the puncture point of a needle 26 as shown, for example, in FIG. 2F, will show that rather than cutting a single large flap 16BF of container material 16BM when penetrating the wall of a container 16, as in the case of a needle 26, a pyramidal puncture point 36P will form openings bounded by three or four small flaps through the walls of a container 16, depending on the number of faces of the pyramid.

It is anticipated that the use of a pyramidal puncture port will reduce the probability of one or more broken off container wall material 16MB flaps blocking the transport of medication and air from the container 16 to the patient being taken up by the patient together with the medication. It will be recognized, however, that the choice of a needle 26 or a needle 36 for a given inhaler 10 will often be determined by the dimensions and material or materials comprising the container 16, and that each design of needle will be advantageous in certain circumstances.

Lastly in this regard, it will be noted that a pyramidal needle 36 is illustrated in FIGS. 8C and 8D of being comprised of hollow, tubular body 36B and a separate pyramidal point 36P that is mounted into the end of the body 36B. It will be recognized, however, that a pyramidal needle 36 may be manufactured in a number of alternate ways, including as a pyramidal needle 36 wherein the body 36B and the pyramidal point 36P are formed as a single component. For example, a needle 36 may be manufactured by an injection molding process or by a plating molding process wherein a material is plated or otherwise deposited on a mold form. In other example, a single part needle 36 may be fabricated by a process wherein the needle 36 is initially manufactured as a hollow tube with the lower end of the tube subsequently being "notched" into three or four "petals" or triangles that are then crimped or squeezed together to form the pyramidal point, at the same time closing the end of the hollow tube forming the body 36B of the pyramidal puncture point needle 36.

Referring to FIG. 8E, therein is illustrated a yet further embodiment of an inhaler 10 with a yet further alternate embodiment of a medication delivery needle 26, designated as a double medication delivery needle 26XY comprised of an upper delivery needle 26X and a lower delivery needle 26Y. As illustrated therein, the lower end of needle passage 12C, that is, the end of needle passage 12C ending at body chamber 12B terminates in upper delivery needle 26X wherein upper delivery needle 26X extends into body chamber 12B by a distance sufficient to penetrate into the upper end of a container 16 when the inhaler 10 is activated as described herein above. Upper needle 26X may assume any of the needle forms described herein above, such as those illustrated in FIGS. 1B and 8A, and will include an air and medication passage extending through upper needle 26X to the lower end of upper needle 26X to terminate in one or more inlets 26M located at the lower end of the upper needle 26X. Upper needle 26X need not necessarily include one or more air/medication ports 26AM, however, but may do so.

As also illustrated, the lower end of mouthpiece 12 further includes a container support/guide 12D that extends into upper chamber 12B around upper needle 26X to receive, guide and support the upper end of the container 16 during activation of the inhaler 10, when mouthpiece 12 and body 14 are axially telescoped so that double needle 26XY penetrates the ends of the container 16. In a presently preferred embodiment as illustrated in FIG. 8E, the lower surface of container support/guide 12D forms a concave surface shaped at least generally to the shape of the end of the container 16. Container support/guide 12D, and in particular the outer rim portion of container support/guide 12D, extends into upper chamber 12B by a distance sufficient to support and guide the container 16 during the inhaler 10 activation operation, and the length and shape of container support/guide 12D is such as not to interfere with body 14 when the inhaler 10 is activated. In this regard, it will be noted that in the illustrated embodiment the outer diameter of container support/guide 12D is sufficiently large to enclose at least a significant portion of the upper end of the container 16. The outer diameter of container support/guide 12D is less than the inner diameter of upper chamber 12B in the illustrated embodiment, however, to allow a corresponding portion of body 14 to extend into and interlock with mouthpiece 12 in this space, in a manner similar to that illustrated with respect to FIG. 1A. In other embodiments, however, and for example, container support/guide 12D may extend the full width of upper chamber 12D and the length of container support/guide 12D may be such that there will not be interference between mouthpiece 12 an body 14 when the inhaler 10 is activated.

Lower needle 26Y, in turn, terminates lower air passages 18A and 20 and extends upward into into body chamber 12A by a distance sufficient to penetrate into the lower end of container 16 when the inhaler 10 is activated as described herein above. Again, lower needle 26Y may assume any of the needle forms described herein above, such as those illustrated in FIGS. 1B and 8A, and will include an air and medication passage extending through lower needle 26Y to the upper end of lower needle 26Y to terminate in one or more outlets 26M located at the upper end of lower needle 26Y. Also again, lower needle 26Y need not necessarily include one or more air/medication ports 26AM, but may do so.

Lastly, it will be recognized that when an inhaler 10 as illustrated in FIG. 8E is activated by axially telescoping the mouthpiece 12 and body 14, upper and lower needles 26X and 26Y will pierce the enclosed container 16 to form generally the same air/medication passage through the container 16 and to the patient as has been described elsewhere herein above with respect to other forms of the needle 26/36. In this regard, it will be recognized that the implementation illustrated in FIG. 8E differs essentially in that the middle portion of the air/medication passage through container 16 is comprised of container 16 itself, rather than of the body of the needle 26/36. It will also be recognized that the implementation shown in FIG. 8E allows a simpler needle 26XY because the needle is comprised of two short needles rather than one longer and thus mechanically weaker needle. In addition, the use of two shorter needles reduces the requirements for alignment of the needle or needles because each of needles 26X and 26Y needs only to be generally aligned with the axis of the container 16 and chambers 14a and 14B. In implementations using a single longer needle, however, the needle must be aligned along the entire length of chambers 14A and 14B and container 16 so as to penetrate the lower end of the container 16 and enter the lower air passage.

D. Alternate Embodiments

Windowed Inhalers 10

Referring to FIGS. 9A and 9B, therein are illustrated an embodiment of an inhaler 10 having container windows 38A and 38B in, respectively, the side walls of mouthpiece 12 and body 14 to allow visual inspection of the existence and state of a medication container 16 residing in the chamber 14B of body 14. The mouthpiece 12 and body 14 may have matching pairs of windows 38A and 38B located on diametrically opposite one another in mouthpiece 12 and body 14, or may have a single pair of windows 38A and 38B located only on one side of the mouthpiece 12 and body 14. The latter embodiment may require that the body 14 or the body 14 and mouthpiece be comprised of, for example, a transparent or translucent material, to allow sufficient light to enter the chamber 14B to illuminate a container 16 therein, or that the body 14 and mouthpiece 12 have a light port located opposite the windows 38A and 38B for the same purpose.

It will be noted that in the embodiment specifically illustrated in FIGS. 9A and 9B the container widow or windows 38B in body 14 are located directly adjacent chamber 14B and are of a length sufficient to allow a clear view of a container 16 in the chamber 14B. It will also be noted that in this embodiment the window or windows 38A in mouthpiece 12 are located so as to be directly adjacent the window or windows 38B when the inhaler 10 is actuated, that is, when the body 14 has entered mouthpiece 12 to an extent that the medication is released to the patient. This arrangement will allow visual inspection of the actuated inhaler 10 to provide an indication of whether there was a medication container 16 in the inhaler 10 and whether or to what extent the medication therein has been delivered to the patient.

It may also be desirable to allow inspection of, for example, a pre-loaded but not yet actuated inhaler 10, such as an inhaler 10 that has been stored in the pre-loaded state, which would require providing a view of the chamber 14B while the mouthpiece 12 and body 14 were in the non-actuated position. This may be accomplished, for example, by designing the body 14 and mouthpiece 12 so that at least a portion of the window 38B and chamber 14B extend outside the mouthpiece 12 when the inhaler 10 is in the non-actuated position. In other embodiments, such as embodiments wherein chamber 14B is enclosed within mouthpiece 12 in the assembled but non-actuated position, the window 38A in mouthpiece 12 may be extended to overlap the window 38B in body 14 when body 14 is in the non-actuated position. Alternately, the mouthpiece 12 may be provided with two axially spaced windows 38A, one located to correspond with window 38B when body 14 is in the non-actuated position and one located to correspond with window 38B when body 14 is in the actuated position.

It should also be noted that windows 38A and 38B comprised a passage through the walls of mouthpiece 12 and body 14 and into the chamber 14B, which may raise questions of preventing loss of the medication through the windows 38B and 38A or of an unwanted flow of air through the windows and into the chamber 14B. This issue, however, may be addressed in a number of ways, such as sealing the window 38B through the wall of the chamber 14B with a transparent or translucent "window pane", using a container 16 of dimensions and material suitable to provide and preserve the sealing of the chamber 14B, or manufacturing the body 14 of a transparent or translucent material that will pass light while providing a sealed chamber 14B.

E. Alternate Embodiments

Multiple Dose Inhalers 10

As discussed elsewhere herein, an inhaler 10 may also be designed to contain and deliver multiple medication dosages, thereby including a mechanism or structure to hold multiple medication containers and to allow the selection and actuation of individual medication containers. The mechanism for holding and selecting among multiple medication containers may, for example, assume the form of a magazine or clip inserted into the body 14, such as used to load cartridges into firearms, or the body 14 may itself contain multiple chambers 14B, similar to the chambers in a revolver cylinder. In this case of a magazine or clip mechanism the entire clip or magazine could be provided with an overpack to provide the necessary shelf life, or the individual containers could be contained in individual overpacks. In the case of a revolver cylinder arrangement with multiple chambers 14B it would be possible to provide each medication container 16 with an individual overpack, or the body 14 with the medication containers 16 therein could be provided with an overpack. It will be recognized, in this regard, that those implementations of a clip or magazine or a body 14 with an overall overpack, as opposed to individual overpacks for the individual containers 16, it would be necessary to use all of the dosages within the "opened package" shelf life.

Figure 10A:
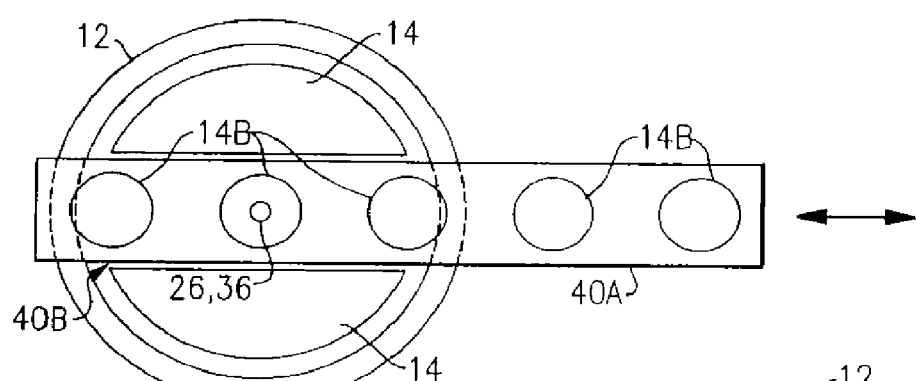
FIG. 10A is a diagrammatic end view illustration of an inhaler accepting a linear magazine containing multiple chambers and containers.

Examples of such embodiments of an inhaler 10 are illustrated in FIGS. 10A through 10D wherein FIG. 10A is a diagrammatic end view illustration of an inhaler 10 accepting a linear clip or magazine 40A containing multiple chambers 14B and corresponding containers 16. As shown therein, mouthpiece 12 and body 14 include a magazine slot 40B axially traversing mouthpiece 12 and body 14 at the axial location occupied by the chamber 14B in the previously described embodiments of an inhaler 10. That is, so that the needle 26/36 is short of the container 16 in the chamber 14B currently aligned with the needle 26/36 when the body 14 is in the non-actuated position with respect to mouthpiece 12 and so that the needle 26/36 will penetrate the container 16 when body 14 is moved to the actuated position with respect to the mouthpiece 12. As will be apparent from FIG. 10A, individual containers 16 may be selected and used in any order by sliding the magazine 40A along magazine slot 40B until the desired chamber 14B and container 16 are axially aligned with the needle 26/36.

Figure 10B:
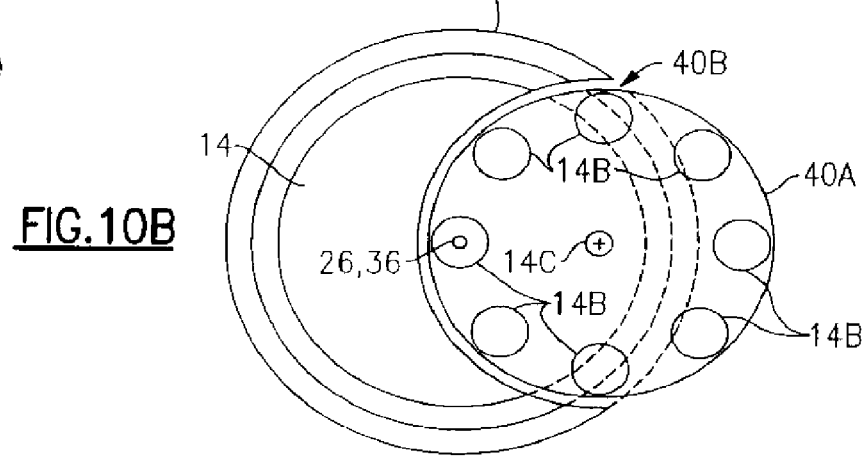
FIG. 10B is a diagrammatic end view illustration of an inhaler accepting a rotary magazine having multiple chambers and containers.

FIG. 10B is a diagrammatic end view illustration of an inhaler 10 generally similar to that of FIG. 10A except that magazine 40A is formed into a circular structure rotating about a longitudinal axis 40C, or axle, located, for example, one an outer rim of body 14 and magazine a lot 40B is correspondingly shaped to accept and support the magazine 40A. In this embodiment, therefore, the magazine 40A is rotated rather than linearly slid to bring the individual chambers 14B and the individual containers 16 therein into axial alignment with the needle 26/36, thereby comprising a revolver cylinder type mechanism.

Figure 10C:
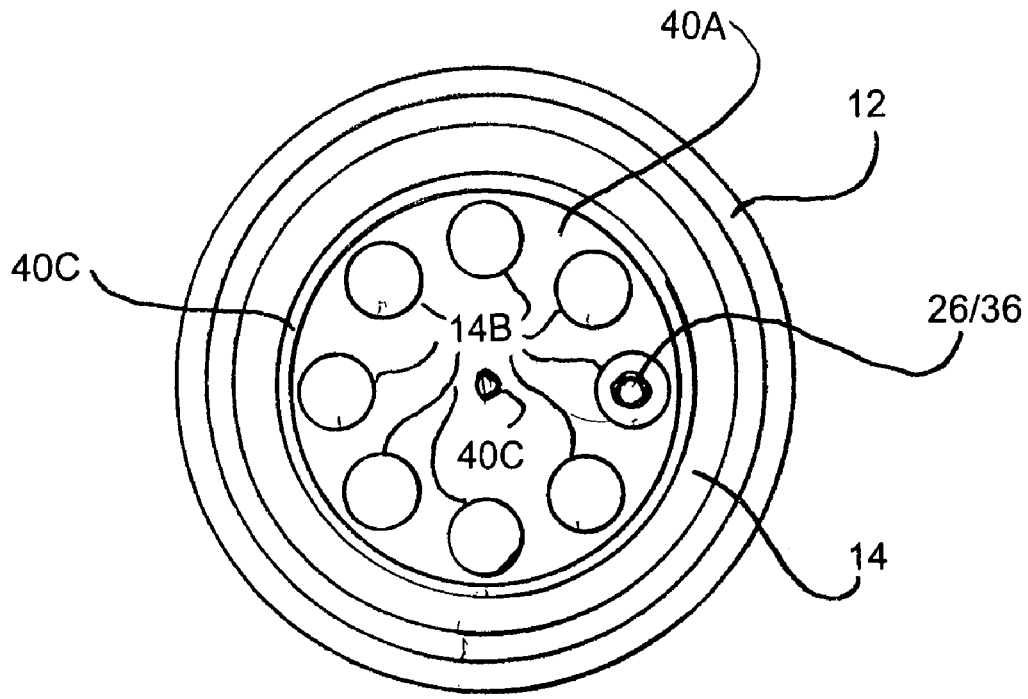
FIG. 10C is a diagrammatic end view illustration of an inhaler having a cylindrical magazine having multiple chambers and containers; and, FIG. 10D is a diagrammatic side view illustration of a multiple medication inhaler.

FIG. 10C is a diagrammatic end view illustration of an inhaler 10 having a cylinder-like magazine 40A wherein the magazine 40A rotates about an axis 40C that is coaxial with the central axis of the body 14 and mouthpiece 12 so that the chambers 14B and containers 16 therein rotate about the outer rim of the body 14. In this implementation, the needle 26/36 and air passages described herein above are offset toward the outer circumference of the body 14 and mouthpiece 12 so that the individual chambers 14B and the containers 16 therein are brought into alignment with the needle 26/36 by rotation of the magazine 40A about the centrally located axis 40C. It will be noted that in the implementation the air/medication passage to and through mouthpiece 12 will typically be directed or bent away from the periphery of the body 14/mouthpiece 12 assembly to align generally with the central axis of the mouthpiece 12 to thereby pass to the patient along the central axis of the mouthpiece 12.

Figure 10D:
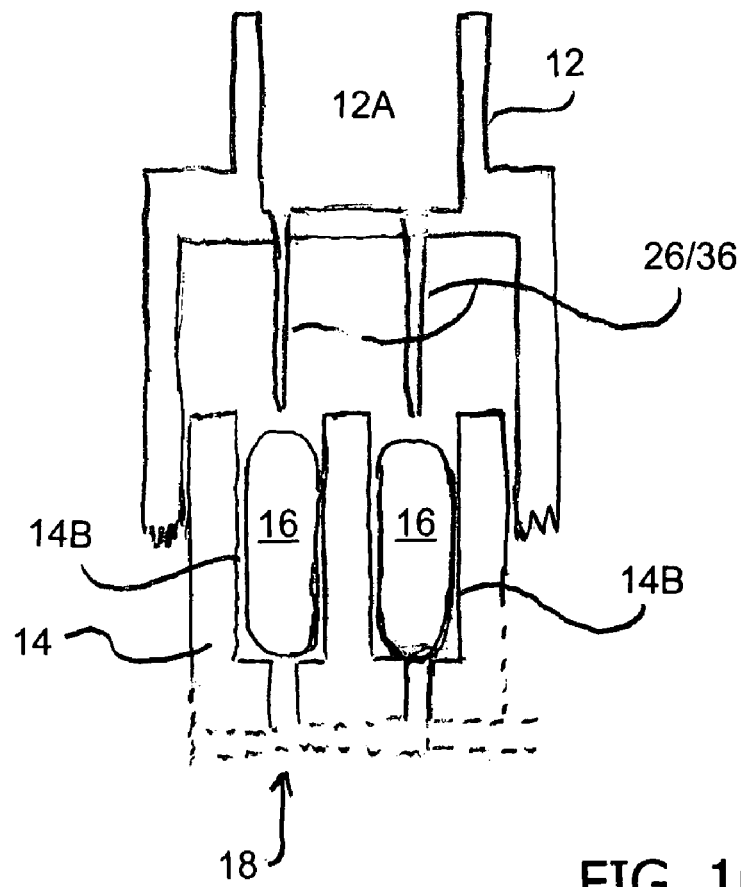

Lastly, FIG. 10D is a diagrammatic side view illustration of a multiple medication inhaler 10 capable of simultaneously delivering a plurality dosages of medications to a patient in a single actuation wherein the medications in the chambers 14B may each be different from one another, or wherein two or more chambers 14B may contain the same medication. It will also be apparent that not all of the chambers 14B must contain medication at a given time and for a given actuation, but it may be preferable to "blank off" the unused chambers 14B to control the air flow through the unused chambers 14B, such as by "dummy" containers 16 or by plugs inserted into the unused chambers 14B.

As illustrated therein, body 14 contains a plurality of container chambers 14B arrange in any manner to accommodate the desired number of chambers 14B withing the body 14. The illustrated example includes two chambers 14B arranged in parallel, but it will be recognized that other embodiments may include a larger number of chambers 14B arranged, for example, in a triangular pattern or a circle. As also shown, each container chamber 14B may have an individual air passage 18 for drawing outside air into and through the chamber 14B or wherein, in other embodiments, the air passages 18 of the chambers 14B may be joined into a single air passage 18 serving all of the chambers 14B. The mouthpiece 12 of the multiple medication inhaler 10, in turn, will include a corresponding plurality of needles 26/36 and air/medication passages connecting the chambers 14B with the mouthpiece chamber 12A.

As may be seen from FIG. 10D, therefore, actuation of multiple medication inhaler 10 will result in the simultaneous opening of the containers 16 residing in the chambers 14B so that the patient will then concurrently receive medication from each of the containers 16.

X. Detent Mechanism

As discussed herein above, an inhaler 10 of the present invention may include a detect mechanism 28 to hold mouthpiece 12 and body 14 in the "open" position until it is desired to activate the inhaler 10, thereby, for example, allowing the inhaler 10 to be pre-loaded and stored for subsequent use or to be handled safely after loading. Referring lastly to the detent mechanisms 28S of the illustrated embodiment, it will be seen in FIGS. 6A-6C that the detent mechanisms 28S are embodied in a resiliently biased tooth and notch structure that includes opposing paired resiliently biased detent hooks 28H that engage with opposing paired detent notches 28N at two locations along mouthpiece 12. As shown in FIGS. 6A and 6C, one pair of detent notches 28N is located at the position corresponding to detent hooks 28H when the inhaler 10 is in the stored state, that is, when the inhaler 10 is loaded with a container 16 and assembled, but not yet activated, and retains body 14 in the stored position with respect to mouthpiece 12. The second pair of detent notches 12N is located at the position corresponding to the location of detent hooks 28H when the inhaler 10 is in the activated state, that is, when body 14 gas been moved into mouthpiece 12 so that needle 36 pierces the container 16 to provide access to the medication therein, and retains mouthpiece 12 and body 14 in the activated state. It must also be recognized with respect to detent mechanisms 26S, however, that any of a wide range of detent types and arrangements are well known in the arts and may be used in place of that illustrated herein.

Since certain changes may be made in the above described improved medication inhaler, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A medication inhaler comprising:
   an inhaler body having: a medication container chamber for receiving and retaining a medication container therein,
   at least one air passage connecting the medication container chamber with exterior air, and
   a mouthpiece axially engageable with the inhaler body and having
      a mouthpiece chamber for communication with a patient's respiratory system, and
      a hollow medication delivery needle communicating with the mouthpiece chamber and extending toward the medication container chamber and having a passageway extending from an air inlet opening, formed in a leading end of the hollow medication needle, to the mouthpiece chamber and at least one air/medication port being formed in an intermediate section of the hollow medication needle for passing the exterior air and medication, from an interior space of a medication container when the medication container is contained within the medication container chamber, through the needle and to the mouthpiece chamber,
      wherein the mouthpiece engages with the inhaler body in
         a first position in which the needle extends into the medication container chamber short of the medication container, when the medication container is contained within the medication container chamber, and
         in a second position in which the needle axially traverses the medication container, when the medication container is contained within the medication container chamber, so that the at least one air/medication port in the needle communicates with the at least one air passage and the interior space of the medication container in the medication container chamber,
      at least one vent passage, extends between the exterior air and the mouthpiece chamber, for supplying the exterior air to the mouthpiece chamber which bypasses the needle and increases airflow through the medication inhaler,
   the needle includes
      a hollow cylindrical body terminating in a puncture end in which the puncture end comprises a puncture point,
      a puncture plane extending obliquely across a diameter of the cylindrical body at an end of the needle toward the medication container,
         the puncture plane defining the puncture point at the end of the needle and puncture edges extending along a plane of intersection between the puncture plane and the cylindrical body, the puncture edges forming an oval opening into the interior of the needle and including cutting edges extending from the puncture point for a first part of the puncture edges and anti-coring edges for a second part of the puncture edges so that when the mouthpiece and the inhaler body are moved from the first position to the second position, the puncture point establishes an initial opening through a wall of the medication container, the cutting edges penetrate the wall of the medication container and separates an attached flap of medication container material from the wall of the medication container, and the anti-coring edges contact the wall of the medication container and push the attached flap of the medication container aside thereby forming an opening through the wall of the medication container so that the wall material of the opening remains attached to the wall of the medication container;

the at least one air/medication port is formed in a surface of the needle such that when the mouthpiece and the inhaler body are in the second position, a first part of a length of the air/medication port is located within the medication container and a second part of the length of the air/medication port is located outside of the medication container and communicates with the air passage which connects the medication container chamber with the exterior air, and the first part of the length of the air/medication port is greater than the second part of the length of the air/medication port.

2. The medication inhaler of claim 1, further comprising:
a detent mechanism for retaining the mouthpiece and the inhaler body
in the first position for storing the medication inhaler with a medication container loaded into the medication container chamber, and
in the second position when the medication inhaler is actuated to deliver the medication to the patient's respiratory system.

3. The medication inhaler of claim 1, wherein the at least one air/medication port located along the medication needle comprises:
at least one pair of diametrically opposed air/medication ports.

4. The medication inhaler of claim 1, further including:
a plurality of vent passages to provide a flow of exterior air into the mouthpiece chamber which bypasses the needle.

5. The medication inhaler of claim 4, wherein the mouthpiece further comprises:
a medication container support/guide extending into the mouthpiece chamber to support the medication container when the mouthpiece and the inhaler body move from the first to the second position.

6. The medication inhaler of claim 1, wherein the needle comprises:
an upper needle communicating with the mouthpiece chamber and extending into the medication container chamber, and
a lower needle communicating with the at least one air passage and extending into the medication container chamber, and when the mouthpiece and the inhaler body are in the second position, the upper and the lower needles respectively penetrate an upper and a lower end of the medication container to form an air and medication passage between the at least one air passage, the interior space of the medication container and the mouthpiece chamber.

7. The medication inhaler of claim 1, wherein the medication container comprises one of:
a capsule,
a blister pack,
a molded container, and
a frangible pellet.

8. The medication inhaler of claim 1, further comprising:
a container magazine having a plurality of medication chambers for each receiving a medication container therein, and
a magazine slot in the inhaler body for receiving the container magazine, wherein
the container magazine is adjustable within the magazine slot to selectively position at least one selected medication chamber and a medication container therein in alignment with the needle.

9. The medication inhaler of claim 1, wherein the at least one vent passage passes through the inhaler body, between the medication container chamber and an outer surface of the inhaler body, and communicates with the exterior air, and
the mouthpiece has at least one mouthpiece passage communicating with the at least one vent passage.

10. A multiple medication inhaler comprising:
an inhaler body having;
a plurality of medication container chambers for each receiving and captively retaining at least one medication container therein,
at least one air passage connecting each medication container chamber with a source of external air, and
a mouthpiece axially engageable with the inhaler body and having
a mouthpiece chamber for communication with a patient's respiratory system, and
a plurality of hollow medication delivery needles communicating with the mouthpiece chamber, each needle extending toward a corresponding medication container chamber and having a passageway extending from an air inlet opening, formed adjacent a leading end of the hollow medication needle, to the mouthpiece chamber and at least one air/medication port being formed in an intermediate section of each of the hollow medication needles for passing exterior air and medication from an interior space of a respective medication container, when a medication container is contained within the respective medication container chamber, and through the needle and to the mouthpiece chamber,
wherein the mouthpiece engages with the inhaler body in
a first position in which the medication needles extend into the respective medication container chambers short of the medication containers, when the respective medication container is contained within the respective medication container chambers, and
in a second position in which at least one needle axially traverses a respective medication container so that the at least one air/medication port in at least one of the needles communicates with the at least one air passage and the interior space of the respective medication container, and the at least one air/ medication port of each needle is formed in a surface of the respective needle such that when the mouthpiece and the inhaler body are in the second position, a first part of a length of the air/medication port is located within the respective medication container and a second part of the length of the air/medication port is located outside of the medication container and communicates with the air passage which connects the medication container chamber with the exterior air, the first part of the length of the air/medication port is greater than the second part of the length of the air/medication port, and at least one vent passage extends between the exterior air and the mouthpiece chamber, for supplying the exterior air to the mouthpiece chamber which bypasses the needles but increases airflow through the medication inhaler.

11. A medication inhaler comprising:

an inhaler body and a mouthpiece which are axially movable relative to one another from a first position to a second position;

the inhaler body having a medication container chamber for receiving and retaining a medication container therein, and at least one air passage coupling the medication container chamber with a source of exterior air;

the mouthpiece having a mouthpiece chamber for communicating with a patient's respiratory system; and a hollow medication delivery needle coupling the mouthpiece chamber with the medication container chamber, the needle having at least one air/medication port therein for communicating with an interior space of a medication container contained within the medication chamber and supplying medication therefrom through the needle and to the mouthpiece chamber;

the needle being spaced from the medication container when the mouthpiece and the inhaler body are in the first position; and, the needle axially traversing a medication container contained within the medication container chamber when the mouthpiece and the inhaler body are moved to the second position, so that the at least one air/medication port in the needle communicates with the at least one air passage and the interior space of the medication container for supplying the medication to the patient; and at least one vent passage bypassing the needle and coupling the exterior air to the mouthpiece chamber for supplying the exterior air to the mouthpiece chamber and increases airflow to the mouthpiece chamber, wherein the needle includes a hollow, tubular body, and a pyramidal puncturing point closing a leading end of the hollow, tubular body, the tubular body has the at least one air/medication port formed therein so that when the mouthpiece and the inhaler body are moved from the first position to the second position the at least one air/medication port in the tubular body communicates with both the at least one air passage and the interior space of the medication container, the at least one air/medication port is formed in a surface of the needle such that when the mouthpiece and the inhaler body are in the second position, a first part of a length of the air/medication port is located within the medication container and a second part of the length of the air/medication port is located outside of the medication container and communicates with the air passage which connects the medication container chamber with the exterior air, and the first part of the length of the air/medication port is greater than the second part of the length of the air/medication port.

12. The medication inhaler of claim 11, further comprising:

a detent mechanism for retaining the mouthpiece and the inhaler body in the first position for storing the medication inhaler with a medication container loaded into the medication container chamber, and in the second position when the medication inhaler is actuated to deliver the medication to the patient's respiratory system.

13. The medication inhaler of claim 11, further including:

a plurality of vent passages to provide a flow of exterior air into the mouthpiece chamber which bypasses the needle.

14. The medication inhaler of claim 11, wherein the at least one vent passage passes through the inhaler body, between the medication container chamber and an outer surface of the inhaler body, and communicates with the exterior air, and the mouthpiece has at least one mouthpiece passage communicating with the at least one vent passage.

* * * * *